(12) United States Patent
Lee

(10) Patent No.: US 9,655,686 B2
(45) Date of Patent: May 23, 2017

(54) AUTOMATED STEREOTACTIC APPARATUS

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 158 days.

(21) Appl. No.: 14/462,320

(22) Filed: Aug. 18, 2014

(65) Prior Publication Data

US 2016/0045222 A1    Feb. 18, 2016

(51) Int. Cl.
*A61B 19/00* (2006.01)
*A61B 90/11* (2016.01)
*A61B 17/34* (2006.01)

(52) U.S. Cl.
CPC ....... *A61B 90/11* (2016.02); *A61B 2017/3409* (2013.01); *A61B 2017/3413* (2013.01)

(58) Field of Classification Search
CPC ............ A61B 17/3468; A61B 17/3494; A61B 17/3403; A61B 2017/3413
USPC .......................................................... 606/130
See application file for complete search history.

(56) References Cited

U.S. PATENT DOCUMENTS

| | | | |
|---|---|---|---|
| 5,623,931 A | 4/1997 | Wung | |
| 5,941,889 A | 8/1999 | Cermak | |
| 6,203,499 B1 | 3/2001 | Imling | |
| 6,475,152 B1 | 11/2002 | Kelly, Jr. | |
| 6,485,426 B2 | 11/2002 | Sandhu | |
| 7,691,066 B2 | 4/2010 | Kosaku | |
| 7,846,103 B2 | 12/2010 | Cannon, Jr. | |
| 7,976,469 B2 | 7/2011 | Bonde | |
| 8,057,487 B2 | 11/2011 | Chu | |
| 8,073,592 B2 | 12/2011 | Cermak | |
| 8,118,743 B2 | 2/2012 | Park | |
| 8,216,149 B2 | 7/2012 | Oonuki | |
| 8,241,301 B2 | 8/2012 | Zhang | |
| 8,257,264 B2 | 9/2012 | Park | |
| 8,496,593 B2 | 7/2013 | Park | |
| 8,521,257 B2 | 8/2013 | Whitcomb | |
| 8,574,160 B2 | 11/2013 | Gorzitze | |
| 8,706,186 B2 | 4/2014 | Fichtinger | |
| 2002/0058872 A1 | 5/2002 | Steininger | |
| 2005/0234435 A1* | 10/2005 | Layer | A61B 17/3403 606/1 |
| 2007/0073155 A1 | 3/2007 | Park | |
| 2011/0112549 A1* | 5/2011 | Neubach | A61B 8/485 606/130 |
| 2011/0313293 A1 | 12/2011 | Lindekugel | |
| 2012/0059260 A1 | 3/2012 | Robinson | |
| 2013/0066192 A1 | 3/2013 | Sarvestani | |
| 2013/0197355 A1 | 8/2013 | Lee | |
| 2013/0225984 A1 | 8/2013 | Cheng | |

\* cited by examiner

*Primary Examiner* — Tuan V Nguyen

(57) ABSTRACT

The present invention presents an apparatus and methods to stereotactically guide and automatically insert an invasive tubular device to a tissue object of a living body. The apparatus comprises a stereotactic positioning assembly and a powered propulsion assembly that controllably drives an invasive tubular device in and out of a tissue object. The stereotactic positioning assembly encloses an ultrasound transducer to visualize and aim at the tissue object, and adjusts an insertion angle of the invasive tubular device coupled with the powered propulsion assembly.

15 Claims, 14 Drawing Sheets

A

B

Figure 10
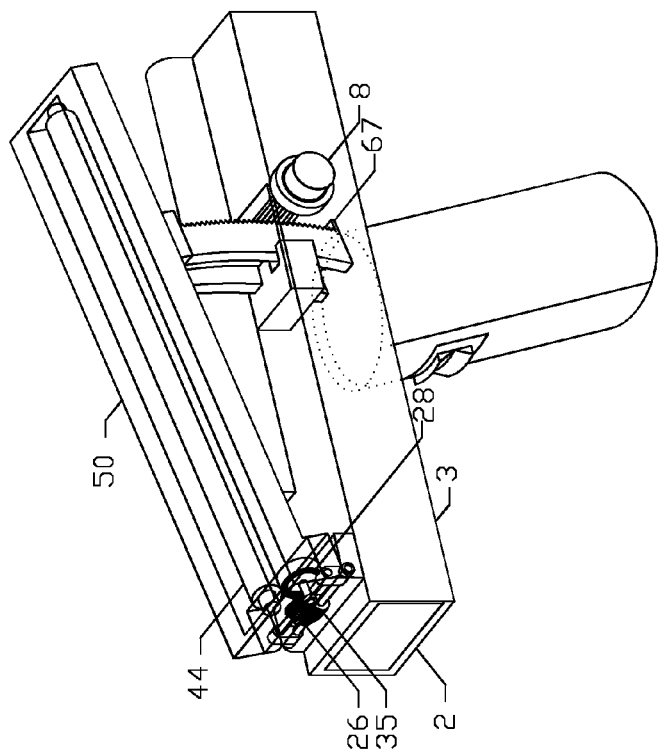
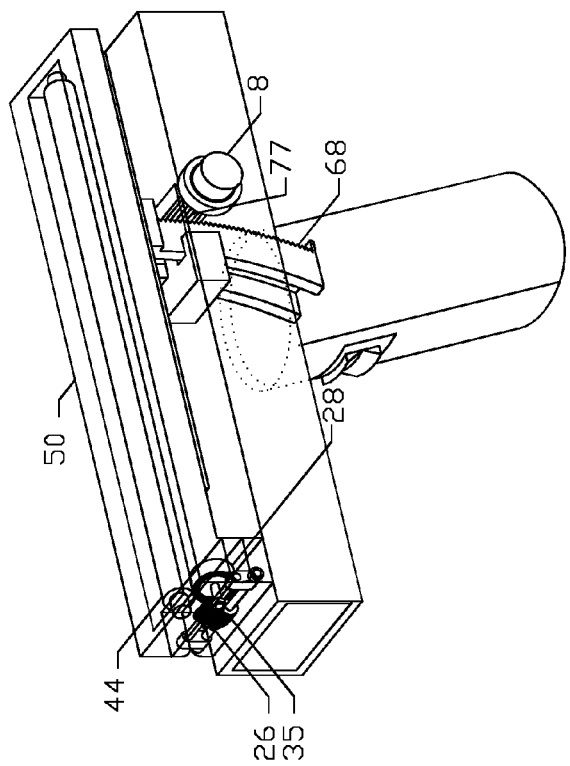

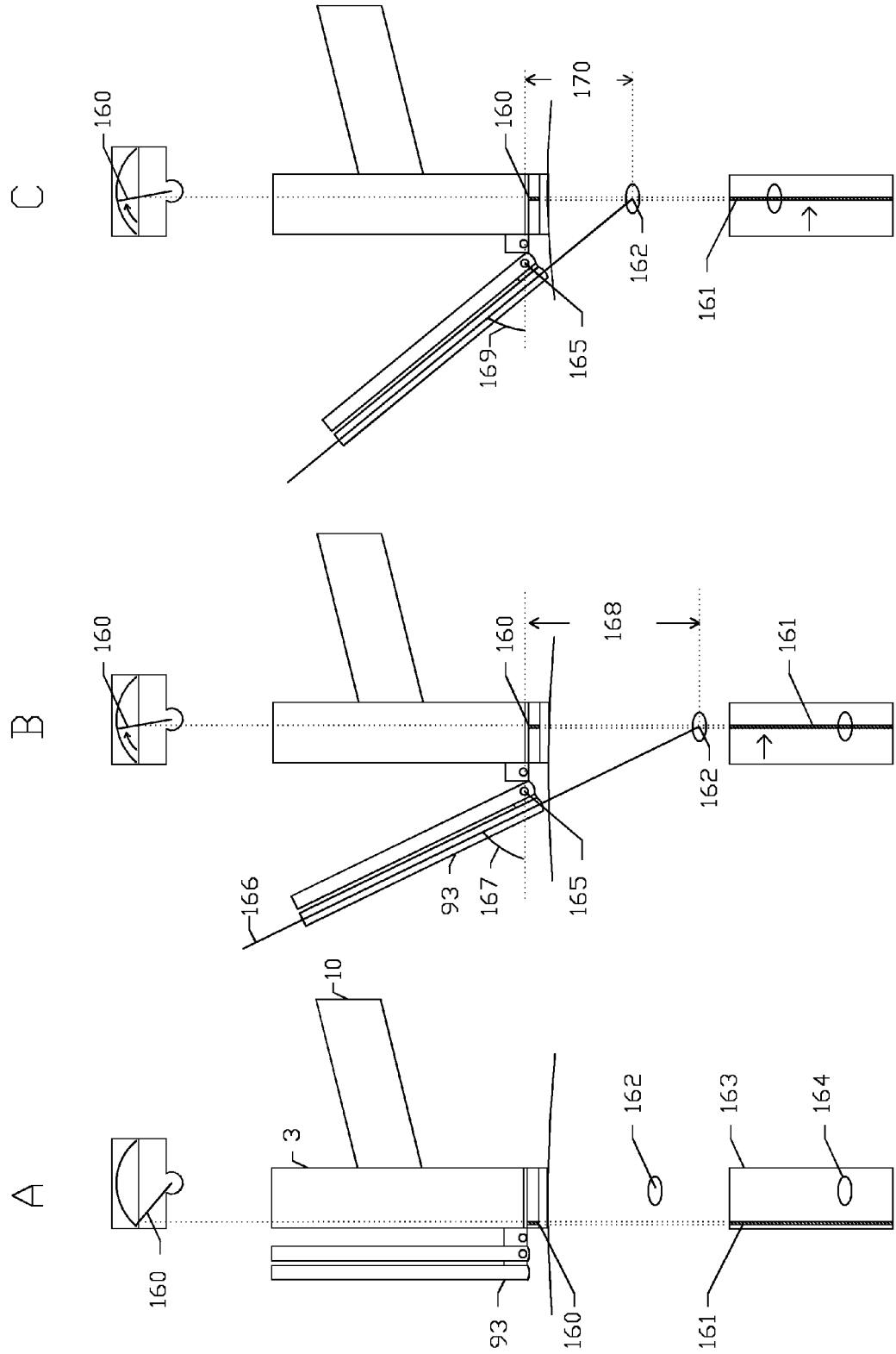

AUTOMATED STEREOTACTIC APPARATUS

STATEMENT REGARDING FEDERALLY SPONSORED RESEARCH OR DEVELOPMENT

The present invention is not a federally sponsored research or development.

TECHNICAL FIELD

The present invention relates generally to the field of introduction of invasive tubular devices to a living body for medical purposes. More specifically, the present invention provides a powered apparatus and methods to stereotactically guide and automatically insert an invasive tubular device into a tissue using ultrasound.

BACKGROUND OF THE INVENTION

An invasive tubular device can be guided to reach a tissue object under ultrasonographic visualization by an apparatus that measures an insertion angle and a depth. Insertion angle of an invasive tubular device can be adjusted to various positions of an ultrasound transducer in relation to a center of the tissue object. The apparatus adjusts angulation of the invasive tubular device by using ultrasonographic visual information of a set of insertion angle and depth of the invasive tubular device to reach the tissue object. One major drawback of the apparatus is a necessity to insert an invasive tubular device manually while visualizing insertion procedures. In-process visualization of insertion procedures of invasive devices is especially important for small lesions, lesions located deep in a body, lesions located near vital structures or lesions that move during invasive procedures by physiologic bodily function such as breathing, heartbeat or pulsating blood vessels, to increase accuracy of the insertion and to reduce chances of potential complications of the procedure. Manual procedures are well-known for their unpredictability and variability of successful outcome, whether it is for inserting an invasive tubular device, for obtaining a tissue sample or for marking a particular site for further interventions. Although stereotactic placement of an invasive tubular device by in-process ultrasound visualization would reduce the unpredictability and variability to an extent, it would continue to be an important issue as long as the invasive tubular device is manually handled by a human operator whose prior experiences and technical dexterity would vary.

This technical challenge by a human factor may be overcome if stereotactic placement of an invasive tubular device would be automated and powered by an apparatus which minimizes operator's input. The apparatus may be operable by a single hand of an operator, which monitors a procedure real-time and consistently produces an expected range of successful outcome of the procedure. Simple mode of automated operations by the apparatus makes procedural success depend less on an operator but more on accuracy and reliability of the apparatus. Success rate of procedures would go higher if the apparatus requires less input, has less interactive components for optimum performance and has fail-safe safety measures to prevent unintended harm to a subject undergoing invasive procedures. A minimum set of input for correct positioning of an invasive tubular device would require a two-dimensional insertion angle and depth of the invasive device to reach a tissue object, which can be verifiably obtainable by our prior inventions using real-time ultrasonographic visualization of a tissue object. Two-dimensional measurements and visualizations are advantageous to three-dimensional ones since the vast majority of current imaging displays are two-dimensional. Three-dimensional targeting of an object in a two-dimensional display system requires separate and significant training on the part of an operator since human perception of a depth at an angle to a two-dimensional panel of display is not natural.

A minimum set of device assemblies would include a stereotactic positioning system, a powered propulsion system of an invasive tubular device and a non-reusable invasive tubular device. The powered propulsion system should deliver adequate forward and backward linear force to an invasive device for its penetration into and retrieval from a tissue. It should be instantaneously controllable for introduction of the invasive device into a tissue to avoid harm to vital structures such as blood vessels. These may be accomplished by using a design to convert rotational torque to linear displacement for propulsion at a range of ratio between rotational and linear displacements. A propulsion force and a degree of precision of control of linear displacement of an invasive tubular device increase on a higher number of rotations per a unit of linear displacement. The apparatus should be configured for fail-safe measures for safety, the most important of which is to limit penetration of an invasive tubular device into a tissue. Unintended penetrations and blind operations are most commonly associated with procedural complications such as puncturing blood vessels and various natural body cavities. Degree of ease in withdrawing the invasive tubular device is equally important as well since even a well thought-out pre-procedure planning may sometimes turn out to be inadequate to deal with unpredictable nature of a human body. These would be addressed by in-process visualization of the procedures and full controllability of linear movement of an invasive tubular device.

SUMMARY OF THE INVENTION

The present invention provides a powered apparatus that stereotactically guides and automatically introduces an invasive tubular device to a tissue object with ultrasonographically visualized targeting approaches. The apparatus provides a positioning means to rotationally adjust insertion angle of an invasive tubular device to reach the tissue object in an ultrasonographic field and a powered means to linearly introduce invasive tubular devices to the tissue object. The apparatus comprises a positioning assembly, a powered propulsion assembly and an invasive tubular device assembly. The positioning assembly encloses an ultrasound transducer and coordinates adjusting an insertion angle of an invasive tubular device with arranging a visualizable linear alignment between a point of a transducer head and a tissue object in an ultrasonographic field. The propulsion assembly, powered by an electric servomotor, converts rotational torque through gear systems to linear to and fro movement for an invasive tubular device and controllably drives the invasive tubular device toward and away from the tissue object. The invasive tubular device assembly releasably carries an invasive tubular device, has a mechanism to limit linear movement of the invasive tubular device and is reversibly anchorable to the propulsion assembly. The invasive tubular device can be configured for single axial penetration or double coaxial sequential penetration into the tissue object.

In one embodiment, the present invention is provided as a hand-held apparatus which comprises a positioning assembly housed in a principal enclosure, a propulsion assembly and an invasive tubular device assembly. The principal enclosure houses an electromagnetic device of the positioning assembly and an ultrasound transducer, a servomotor and gearbox assembly to generate and transmit rotational torque and a power and electronic control assembly, arranged in tandem. The principal enclosure is configured to be connected to a handle, located below a lower wall of the principal enclosure, through which cables of the apparatus pass to a main ultrasonographic machine. On an upper wall of the principal enclosure, a proximal portion of the principal enclosure adjoins a pivotable transverse parallel shaft gear assembly which includes a proximal part of the propulsion assembly. The pivotable transverse parallel shaft gear assembly is controllably pivotable by a rack and pinion gear assembly which is housed in the principal enclosure in a distance from said pivotable transverse parallel shaft gear assembly and is attached to an undersurface of the propulsion assembly. The propulsion assembly is located above the principal enclosure aligned along a longitudinal axis of the principal enclosure and is pivotably angulatable about a pivoting center of the pivotable transverse parallel shaft gear assembly. Angulation of the propulsion assembly relative to a horizontal axis of a proximal end of an ultrasound transducer head inside the principal enclosure is coordinated with ultrasonographically visualizable pointing of a tissue object in an ultrasonographic view by rotation of a pinion gear of the rack and pinion gear assembly which is a part of a positioning assembly. The positioning assembly comprises a position sensor coaxially connected to the pinion of the rack and pinion gear assembly, an electromagnetic pointing device located in front of the ultrasound transducer and an electronic circuit board of the power and electronic control assembly. A non-reusable invasive tubular device assembly is releasably attached to an upper part of the propulsion assembly which controllably provides said invasive tubular device with to and fro linear propulsion. The servomotor and gearbox assembly generate rotational torque and convert said rotational torque to linear propulsion force, which is powered and controlled by the power and electronic control assembly.

In one embodiment, the principal enclosure is provided in one or a plurality of configurations including a longitudinally rectangular tubular configuration which comprises a series of sequentially arranged open individual rectangular slots at a proximal end of said enclosure to house a non-reusable flat solid gel couplant, the electromagnetic pointing device and a second flat solid gel couplant assembled in tandem in front of a face of the ultrasound transducer. The principal enclosure is configured to house the ultrasound transducer in a manner to align longitudinal and horizontal axes of the transducer in parallel with longitudinal and horizontal axes of said principal enclosure, respectively. Both the horizontal and longitudinal axes of the transducer are used as reference axes to calibrate angular displacement of the pivotable transverse parallel shaft gear assembly. A rectangular space is provided behind a distal end of the ultrasound transducer to accommodate the rack and pinion gear assembly. On an undersurface of an upper wall of the rectangular space, there is provided a rack stabilizer to maintain stable vertical movement of a rack of the rack and pinion assembly through an opening on said rectangular space of the upper wall. The pinion is connected to a rotatable control knob which protrudes through a lateral sidewall of the principal enclosure. The servomotor and gearbox assembly is located behind the rack and pinion gear assembly, which transfers rotation to a distal portion of a longitudinal output shaft through a spur-gear arrangement. The longitudinal output shaft is housed in a tubular enclosure adjoining one longitudinal side of an outer surface of the upper wall of the principal enclosure. A proximal end of the longitudinal output shaft is configured as a bevel gear which meshes with a corresponding bevel gear of the pivotable transverse parallel shaft gear assembly. At a distal portion of the enclosure behind the servomotor and gearbox assembly, a rectangular space is provided to accommodate the power and electronic control assembly.

In one embodiment, the pivotable transverse parallel shaft gear assembly is provided in one or a plurality of configurations, which has two sets of transverse shaft spur gears in a vertically stacked-up, parallel meshing arrangement. One example of a configuration of a lower transverse shaft spur gear has a cylindrical spur gear fixedly inserted over a central shaft, which is enclosed in a lower gearbox adjoining the proximal upper wall of the ultrasound transducer enclosure. An upper transverse shaft spur gear is similarly configured and becomes a pivotable transverse shaft spur gear of the propulsion assembly. Both the central shafts are rotatably encased in a parallel shaft gear mount on each end of said shaft in a vertical configuration. Both the parallel shaft gear mounts are fixedly attached to the lower gearbox and maintain a vertically stacked-up meshing configuration of both the lower and upper transverse shaft spur gears. The parallel shaft gear mounts are configured to have a rolling-element bearing joint for each end of said central shaft to reduce rotational friction of central shafts inside said shaft gear mounts.

In one embodiment, the propulsion assembly is provided in one or a plurality of mechanical configurations, which comprises a pivotable upper gear assembly at the proximal end of said propulsion assembly, a helical gear shaft along a longitudinal axis of said propulsion assembly, a propulsion block rotatably placed over the helical gear shaft and a longitudinally rectangular low-profile frame encasing individual components of said propulsion assembly. The pivotable upper gear assembly is provided in one or a plurality of configurations, which comprises a transverse bevel gear coaxially combined with the pivotable transverse shaft spur gear and a longitudinal cylindrical gear complex. The longitudinal cylindrical complex has a spur gear arrangement on an outer cylindrical surface and a planar bevel gear projected proximally from a plane perpendicular to a rotation axis of said longitudinal cylindrical gear complex. The transverse bevel gear of said pivotable transverse shaft gear is configured to mesh at a right angle with the corresponding planar bevel gear of said longitudinal cylindrical gear complex. The cylindrical spur gear of said longitudinal cylindrical gear complex is configured to mesh in parallel with a corresponding spur gear projected from a proximal portion of the helical gear shaft. A rotating center of the pivotable transverse shaft spur gear of said pivotable upper gear assembly is a pivoting center of the propulsion assembly. The upper gearbox enclosing the pivotable upper gear assembly pivots about the rotating center of the pivotable transverse shaft spur gear.

In one embodiment, the lower transverse shaft spur gear is coaxially and fixedly combined with a transverse bevel gear which is configured to mesh at a right angle with the corresponding longitudinal bevel gear projected from the proximal end of the longitudinal output shaft connected to the servomotor and gearbox assembly. Rotational torque generated by the servomotor is transmitted to the longitudinal bevel gear of the longitudinal output shaft, which rotates the transverse bevel gear coaxially attached to the lower transverse shaft spur gear. Rotation of the lower transverse shaft spur gear then rotates the upper pivotable transverse shaft spur gear. Rotation of the transverse bevel gear attached to the upper pivotable transverse shaft spur gear in turn rotates the planar bevel gear of the cylindrical gear complex which ultimately transmits rotation to the proximal spur gear of the helical gear shaft of the propulsion assembly.

In one embodiment, the propulsion assembly is configured to be pivotably angulated about the central shaft of the upper pivotable transverse shaft gear relative to the horizontal axis of the proximal end of the ultrasound transducer head inside the principal enclosure by curvilinear movements of the rack of the rack and pinion gear assembly located in said principal enclosure. The rotatable control knob connected to the pinion rotates said pinion which meshes in parallel with gear teeth of the rack. The rack is configured to be attached to the undersurface of the frame of the propulsion assembly, which raises or lowers said frame at an angle by rotation of the pinion. Rotations of the pinion are monitored by the position sensor coaxially attached to the pinion, which provides the power and electronic control assembly with angular information of the propulsion assembly. The upper transverse shaft spur gear of the pivotable transverse parallel shaft gear assembly maintains the parallel meshing arrangement with the lower transverse shaft spur gear during pivotable angulation of the propulsion assembly. This configuration allows rotational torque from the servomotor to continue to be transmitted to the upper transverse shaft spur gear and then to the proximal spur gear of the helical gear shaft over a range of angulations of the propulsion assembly.

In one embodiment, the propulsion assembly is configured to convert rotational torque of the helical gear shaft to axial movement of the propulsion block of said propulsion assembly. The helical gear shaft runs from one end of the rectangular frame of the propulsion assembly located distal to the proximal spur gear to the other opposite end along a central longitudinal line of said rectangular frame and is configured to circumferentially rotate. The propulsion block is provided in one or a plurality of configurations, which has a longitudinal overtube configuration having internal threads on an inner wall of said overtube, a pair of lower horizontal slide rails with each slide rail axially attached to each opposite side of an outer tubular wall and a upper slide rail separately located above the lower horizontal slide rails on an upper part of said propulsion block. The upper slide rail is configured with a pair of notches along longitudinal lateral edges of said upper slide rail, which provides corresponding ridges of the invasive tubular device assembly with reversible snap-fit attachment. Each lower horizontal slide rail of the propulsion block is configured to slide to and fro in a longitudinal rail slot carved in an inner longitudinal sidewall of the rectangular frame. The helical gear of the helical gear shaft coaxially meshes with the internal threads of the propulsion block. Rotation of the helical gear shaft transmits rotational torque to the internal threads of the propulsion block which moves axially in the longitudinal rail slots.

In one embodiment, the servomotor and gearbox assembly is provided in one or a plurality of configurations including a rectangular box configuration which encloses an electric servomotor, a gearbox and a multi-turn rotary position sensing device such as potentiometer, optical encoder or magnetic encoder. The servomotor is irreversibly fixed to a wall distal to said servomotor and gearbox assembly, with its rotor protruding longitudinally along an axis toward the proximal end of the principal enclosure. A protruded portion of the rotor is configured as a longitudinal spur gear that meshes in parallel with a separate cylindrical spur gear. The cylindrical spur gear is connected to the position sensing device coaxially that measures rotational displacements of said cylindrical spur gear. The multi-turn position sensing device is electronically connected to the power and electronic control assembly that receives an electronic information from said position sensing device of a rotational displacement of the cylindrical spur gear to calculate a longitudinal displacement of the propulsion block of the propulsion assembly. The cylindrical spur gear meshes with a second spur gear that coaxially merges with the longitudinal output shaft located outside the principal enclosure. The output shaft is provided in one or a plurality of configurations and is housed in the gear output shaft enclosure. A switch located on an outer surface of the handle assembly is electrically connected to the power and electronic control assembly, and is configured to turn on for a controllably variable duration and off the servomotor in either forward or backward direction.

In one embodiment, the gear output shaft enclosure is provided in one or a plurality of configurations including a longitudinal tubular structure located on an upper surface of the principal enclosure. The output shaft enclosure has a proximal end having an opening through which the output shaft protrudes and a distal end which provides a central flange to encircle a distal end of the output shaft for axial rotation. The output shaft enclosure is configured to provide a means to reduce rotational friction between the output shaft and the output shaft enclosure, which includes rolling-element bearing portions.

In one embodiment, the positioning assembly is provided in one or a plurality of configurations, which comprises a position alignment assembly, the rack and pinion assembly for positioning control, a power and electronic control assembly, the principal enclosure housing an ultrasound transducer and a handle. The position alignment assembly comprises a rotary position sensor coaxially connected to the pinion of the rack and pinion gear assembly and an electromagnetic pointing device. Both the rotary position sensor and electromagnetic pointing device are connected to the power and electronic control assembly which coordinates both devices. The rotary position sensor includes potentiometer, optical encoder or magnetic encoder, and is electronically connected to the power and electronic control assembly that relays an electronic information from said position sensor of angular displacements of the propulsion assembly to the electromagnetic pointing device. The electromagnetic pointing device is provided in one or a plurality of electromechanical configurations, which is enclosed in a substantially ultrasound-transparent flat rectangular box. The flat rectangular box is configured as leak-proof, is filled with an ultrasound-transparent liquid which is electrically non-conductive. The flat rectangular box is located proximal to the face of the transducer. In one example, the electromagnetic pointing device is configured as a galvanometer-type device that uses varying electric voltage, current or resistance to radially move a linear movable pointer around a center of said device. The linear movable pointer is configured to block ultrasound transmission, which is visualized in an ultrasonographic view. Angulation of the propulsion assembly relative to the horizontal axis of the proximal end of the ultrasound transducer head inside the principal enclosure is coordinated with ultrasonographically visualizable pointing of a tissue object in an ultrasonographic view by the linear movable pointer.

In one embodiment, an invasive tubular device assembly is provided in one or a plurality of configurations, which comprises a rectangular frame, an invasive tubular device connected distally to a coupling block and a depth lock. The rectangular frame is configured with a protective open box shell to hold said invasive tubular device inside said shell, a longitudinal rail guide on each longitudinal sidewall of said open box shell to form a longitudinal rail slot in between of said rail guide and said sidewall to carry both the coupling block and depth lock, a serrated inner surface of each inner longitudinal sidewall of said open box shell for reversible fastening of the depth lock and a tubular conduit in a proximal portion of said rectangular frame for passage of the invasive tubular device toward a tissue object. The open box shell is configured with an open upper portion and a closed bottom wall, which allows biologic materials associated with the invasive tubular device to be contained in said box shell. The rectangular frame is configured with a set of snap-fit ridges protruding downward from proximal and distal portions of said frame to be releasably inserted into corresponding snap-fit notches of the propulsion assembly. On an upper surface of one of the longitudinal rail guides, there is provided a series of distance markings to help measure depth of the invasive tubular device in a tissue. The pair of the longitudinal rail guides adjoin at a right angle an inner transverse sidewall of the proximal end of said invasive tubular device assembly. At a distal end of said invasive tubular device assembly, said pair of the longitudinal guides are connected to each other by a transverse planar bridge under the open box shell but are not connected to a transverse sidewall of the distal end of said invasive tubular device assembly. This configuration allows the invasive tubular device to be releasably removable through the distal end of said invasive tubular device assembly.

In one embodiment, the coupling block of the invasive tubular device assembly is provided in one or a plurality of configurations including a box configuration, which comprises a central portion to fixedly anchor a distal portion of a tubular shaft of said invasive tubular device along a longitudinal axis of said coupling block. Said coupling block also comprises a pair of vertical slide rails adjoining a pair of upper longitudinal side edges, respectively, of the central portion and a pair of snap-fit ridges protruding downward from said vertical slide rails to be inserted into the corresponding snap-fit notches, respectively, of the upper slide rail of the propulsion block of the propulsion assembly. Said pair of vertical slide rails are configured to slide in and out of the longitudinal rail slots of said invasive tubular device assembly. The propulsion block of the propulsion assembly controllably provides the coupling block with to and fro linear propulsion. Forward movement of the coupling block pushes the invasive tubular device through the tubular conduit of the proximal portion of the invasive tubular device assembly toward a tissue object. Once an intended invasive procedure has been accomplished, the propulsion assembly pulls the invasive tubular device back to the distal end of said invasive tubular device assembly to complete a cycle of the procedure.

In one embodiment, the depth lock, provided in one or a plurality of configurations including a box configuration, limits penetration of an invasive tubular device into a tissue and comprises a central portion having a centrally located longitudinal tubular conduit, a rocker-switch-type lock and release lever transversely attached on an upper surface of the central portion, a pair of protuberances fixedly attached to an undersurface of a distal part of the lock and release lever, a pair of vertical slide rails adjoining upper longitudinal side edges of the central portion releasably sliding in and out of the longitudinal rail slots of said invasive tubular device assembly and a pair of horizontal slide rails inwardly projecting from a pair of lower edges of the vertical slide rails, respectively. The horizontal slide rails run below the bottom wall of the open box shell of the invasive tubular device assembly. The longitudinal tubular conduit is configured to let a shaft portion of the invasive tubular device pass back and forth. The protuberances of the lock and release lever are configured to exert an outward pressure on the serrated inner longitudinal sidewalls when lowered into the open box shell, thereby reversibly locking the depth lock in place. Raising back the protuberances by a reverse position of the lock and release lever removes the outward pressure, which unlocks the depth lock from the open box shell. The depth lock also is configured to be releasably removable through the open distal end of the invasive tubular device assembly.

In one embodiment, the invasive tubular device is provided in one or a plurality of configurations including a tubular shaft with a stylet inside said tubular shaft. The stylet may have a biopsy sample notch near a proximal end of said stylet, which is configured to capture a tissue sample by a linear movement of said stylet inside the tubular shaft of the invasive tubular device. In this configuration, both the coupling block and depth lock of the invasive tubular device have a concerted actuator mechanism which fires the stylet into an intended tissue object after the invasive tubular device securely holding the biopsy sample notch of the stylet inside the tubular shaft reached a tissue object site. The coupling block comprises two parts which are arranged in tandem along the longitudinal axis of the invasive tubular device. The first part located distally to the second part is similar to the coupling block described above in configuration except for the central portion fixedly anchoring a distal portion of the stylet instead of the tubular shaft, a distal end of a compression spring fixedly anchored to a front vertical sidewall of the central portion encircles the distal portion of the stylet, and a pivotable separator panel slidably inserted in a rectangular separator slot longitudinally carved in an upper surface of the central portion. The second part located proximal to the first part comprises a central portion which fixedly anchors the distal portion of the tubular shaft along the longitudinal axis, a pair of vertical slide rails adjoining upper longitudinal side edges of the central portion releasably sliding in and out of the longitudinal rail slots of said invasive tubular device assembly and a flat trapezoidal slot carved in an upper surface of the central portion along the longitudinal axis. A distal vertical sidewall of the central portion fixedly anchors a proximal end of the compression spring which exerts outward longitudinal pressure separating both the first and second parts. The tubular shaft of the central portion of the second part is configured as conduit for the stylet to freely move inside said tubular shaft.

In one embodiment, a horizontal width of a proximal transverse edge of the trapezoidal slot of the second part is configured to be narrower than a distal transverse trapezoidal width. A proximal portion of the pivotable separator panel of the first part is configured to be inserted into and reversibly held fast by the corresponding trapezoidal separator slot of the second part. A proximal transverse edge of the pivotable separator has a transverse notch on a lower half, which is configured to let a transverse ridge inserted into said notch and lift up said proximal transverse edge. The pivotable separator panel pivots about a transverse shaft located inside a distal portion of the rectangular separator slot of the first part. The rocker-switch-type lock and release lever of the depth lock is configured with the transverse ridge protruding from a distal transverse edge of said lever, which is releasably insertable into the transverse notch of the proximal transverse edge of the pivotable separator panel to lift up and release the proximal portion of said pivotable separator panel from the trapezoidal separator slot. Once the proximal portion of the pivotable separator panel is lifted up, the first and second parts of the coupling block and the depth block get all stacked up longitudinally along the axis, pushed by the propulsion block of the propulsion assembly, with a proximal end of the first part driven to a distal end of the second part of the coupling block resulting in a collapsed compression spring. Likewise, a proximal end of the second part is pushed to the distal end of the depth block. A longitudinal distance between the first and second parts separated by the pivotable separator panel is equivalent to a length of the biopsy sample notch of the stylet protruded from a proximal tip of the tubular shaft. Following deployment of the stylet to obtain a tissue sample, the first part of the coupling block is driven back distally by the propulsion block to retract the biopsy sample notch portion of the stylet back into the tubular shaft. The compression spring of the second part pushes the first part distally during a distal pull-back of said first part in a way said second part stays abutting the distal end of the depth block, thereby maintaining a steady position of the tubular shaft while the stylet is being retracted.

In one embodiment, the power and electronic control assembly is provided in one or a plurality of configurations including a rectangular box configuration which has an integrated circuit board, a segment digital display, an outer control knob coaxially encircling the rotatable knob of the rack and pinion gear assembly. The outer control knob is connected to the integrated circuit board and a power source. The integrated circuit board of the electronic control assembly is located in the distal portion of the principal enclosure and electronically connected to the segment digital display, the positioning assembly, and the switch of the handle assembly. The segment digital display is configured to be visible on a distal outer surface of the integrated circuit board. The segment digital display shows at least a digitized numerical information about a distance between a position of the ultrasound transducer face placed over the tissue target and said tissue target at a substantially right angle. In one configuration, a compartment for replaceable batteries is located inside the principal enclosure and connects batteries electrically with the integrated circuit board, the segment digital display, the positioning assembly and the switch of the handle assembly.

In another embodiment, the power and electronic control assembly is configured to control movement of the electromagnetic pointing device of the positioning assembly upon an electronic input from the position sensing device coaxially attached to the pinion of the rack and pinion gear assembly. In this configuration, rotation of the pinion translates into ultrasonographically visualizable movement of the linear movable pointer of the electromagnetic pointing device. In a two-dimensional ultrasonographic view, the linear movable pointer is configured to produce a thin vertically linear shadow that can be distinguished readily from surrounding tissue images. Rotation of said pinion is configured to match horizontal movement of said linear movable pointer in ways that a longitudinal axis of an invasive tubular device at an insertion angle in the invasive tubular device assembly crosses a linear shadow at a center of a tissue target in the two-dimensional ultrasonographic view.

In one embodiment, a distance (a) from a point of a proximal end of the transducer to a center of a tissue object is calculated by a placement of the proximal end of the transducer to a skin overlying the tissue object at a substantially right angle. A horizontal distance from a pivoting center of the pivotable transverse parallel shaft gear assembly to a point of a linear movable pointer of the positioning assembly measures as (b). Using a simple trigonometry, a distance (h) of an invasive device from the pivoting center of the pivotable transverse parallel shaft gear assembly to the center of the object equals a square root of $(a^2+b^2)$ and a sine of an angle (a) of the pivotable transverse parallel shaft gear assembly is calculated as a ratio of (a) to (h). The horizontal distance (b) is variable based on a moving position of the linear movable pointer of the positioning assembly. Once the distance (h) is calculated, the depth lock of the invasive tubular device assembly moves by the distance (h) ±a margin of error of distance measurement to a point of the rail guide of the invasive tubular device frame from the distal end of said frame and locks in the open box shell, which prevents further forward movement of the invasive tubular device.

In one embodiment, the outer control knob of the integrated circuit board is configured to provide the integrated circuit board with a numerical information of a measured distance (a) from the center of the tissue object vertically up to a point horizontal to the pivoting center of the pivotable transverse parallel shaft gear assembly. The integrated circuit board calculates an angle (a) based on the distance (a) and directs the pivotable transverse parallel shaft gear assembly to rotate to the angle (a) relative to the horizontal axis of the proximal end of the ultrasound transducer head.

BRIEF DESCRIPTION OF THE DRAWINGS

FIG. 4A represents an upper transverse shaft gear assembly; FIG. 4B shows a lower transverse shaft gear assembly; FIG. 4C shows the pivotable transverse parallel shaft gear assembly encased in a pair of parallel shaft gear mounts; FIG. 4D shows an angulated upper transverse parallel shaft gear assembly maintaining an unchanged meshing arrangement with the lower transverse parallel shaft gear assembly.

FIG. 10 shows a schematic example of angulation of the propulsion assembly.

FIG. 14 depicts a schematic illustration of an example of a method of coordination of an angular rotation of the invasive tubular device assembly with a linear movement of a linear movable pointer of the positioning assembly to aim at a tissue object.

DETAILED DESCRIPTION OF THE DRAWINGS

As described below, the present invention provides an automated and powered apparatus stereotactically targeting a tissue object and methods of use. It is to be understood that the descriptions are solely for the purpose of illustrating the present invention, and should not be understood in any way as restrictive or limited. Embodiments of the present invention are preferably depicted with reference to FIGS. 1 to 14, however, such reference is not intended to limit the present invention in any manner. The drawings do not represent actual dimension of devices, but illustrate the principles of the present invention.

Figure 1:
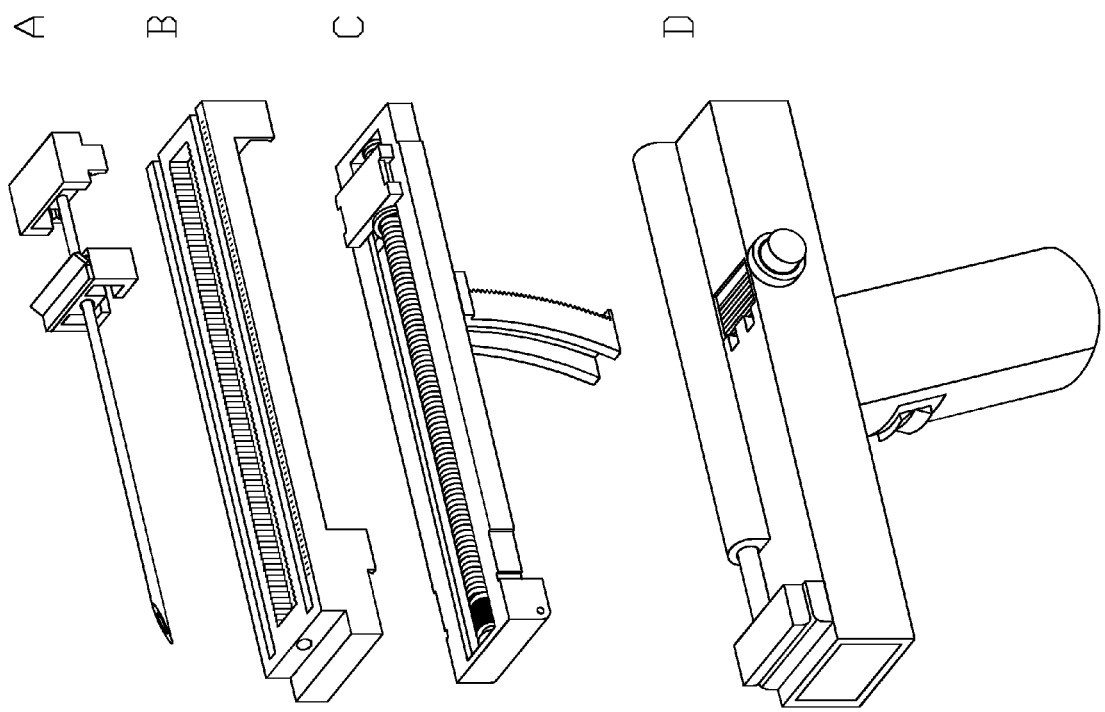
FIG. 1 shows a schematic illustration of an example of an invasive tubular device (A), an invasive tubular device frame (B), a propulsion assembly (C) and a principal enclosure with an output shaft enclosure, a pivotable transverse parallel shaft gear assembly box and a handle (D).

FIG. 1 shows a schematic illustration of an example of the present invention. FIG. 1A represents an invasive tubular device; FIG. 1B represents an invasive tubular device frame; FIG. 1C represents a propulsion assembly; FIG. 1D shows a principal rectangular box enclosure with associated assemblies. The invasive tubular device of 1A is slidably insertable into the the invasive tubular device frame of 1B through an open distal end of said invasive tubular device frame. The invasive tubular device assembly comprising both the 1A and 1B is releasably attachable to the propulsion assembly of 1C. The propulsion assembly of 1C is assembled with the 1D and is pivotable at a proximal end of said propulsion assembly.

Figure 2:
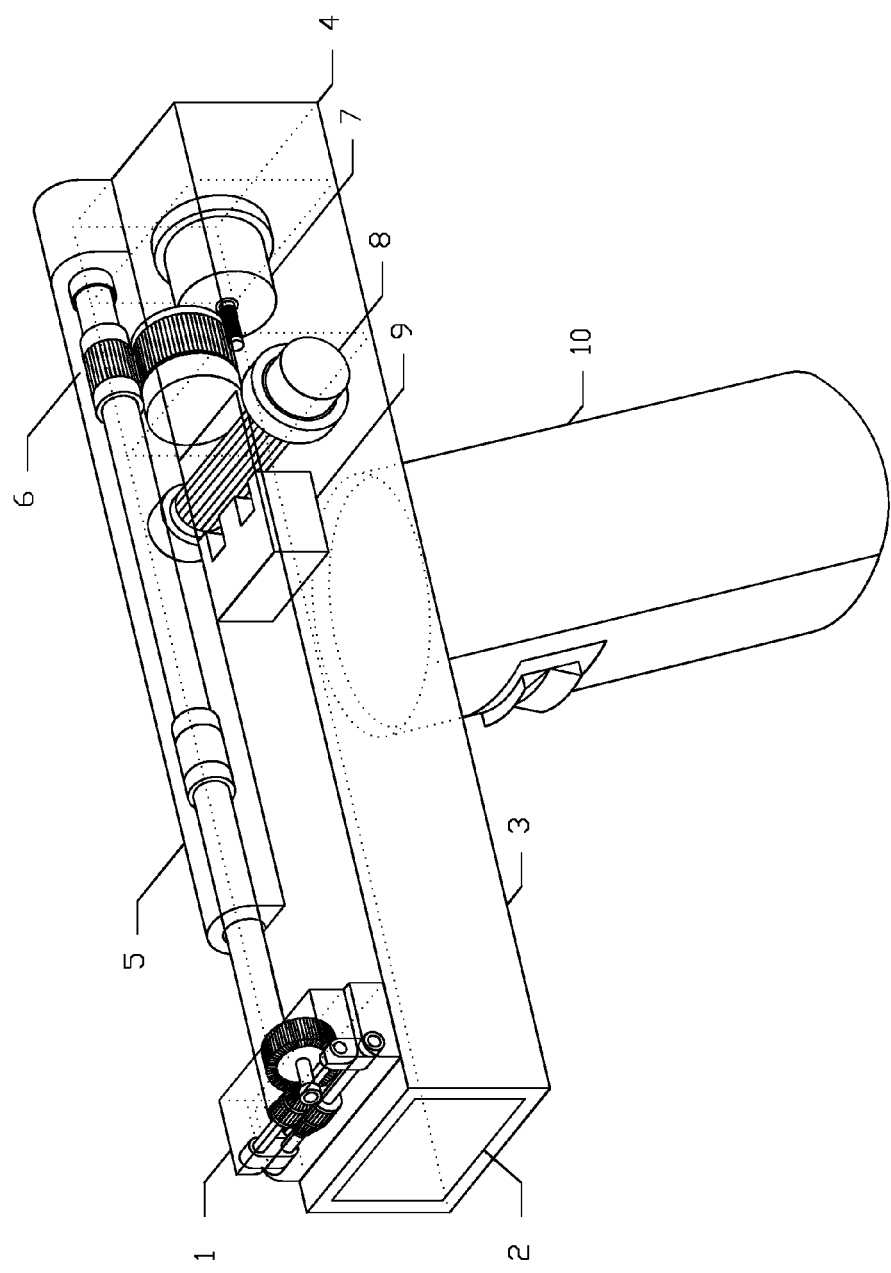
FIG. 2 shows a schematic example of individual components of gear arrangements in and around the principal enclosure.

FIG. 2 shows a schematic example of an overview of gear arrangements enclosed in and attached to the principal enclosure 3. In this particular example, the principal enclosure 3 is configured as rectangular box having a proximal end 2 and a distal end 4. The proximal end 2 of said enclosure is configured as an open window which ultrasound waves pass through and which encloses ultrasound gel couplants and an electromagnetic pointing device. On an upper wall of a proximal portion of the principal enclosure 3, a pivotable transverse parallel shaft gear assembly 1 is attached to an outer surface of said upper wall. Near the distal end 4, there is provided a servomotor and gearbox assembly 6 having a rotating axis of the servomotor 7 arranged longitudinally. The servomotor and gearbox assembly 6 is connected to a distal portion of a longitudinal output shaft enclosure 5 which is attached to one longitudinal side of the upper wall of the principal enclosure 3 and encloses a longitudinal output shaft. In a mid portion of the principal enclosure 3 in front of the servomotor and gearbox assembly 6, there is provided a pinion with a rotatable control knob 8 coaxially attached to said pinion and a rack stabilizer 9. A tubular handle assembly 10 is attached to an open mid portion of a lower wall of the principal enclosure 3.

Figure 3:
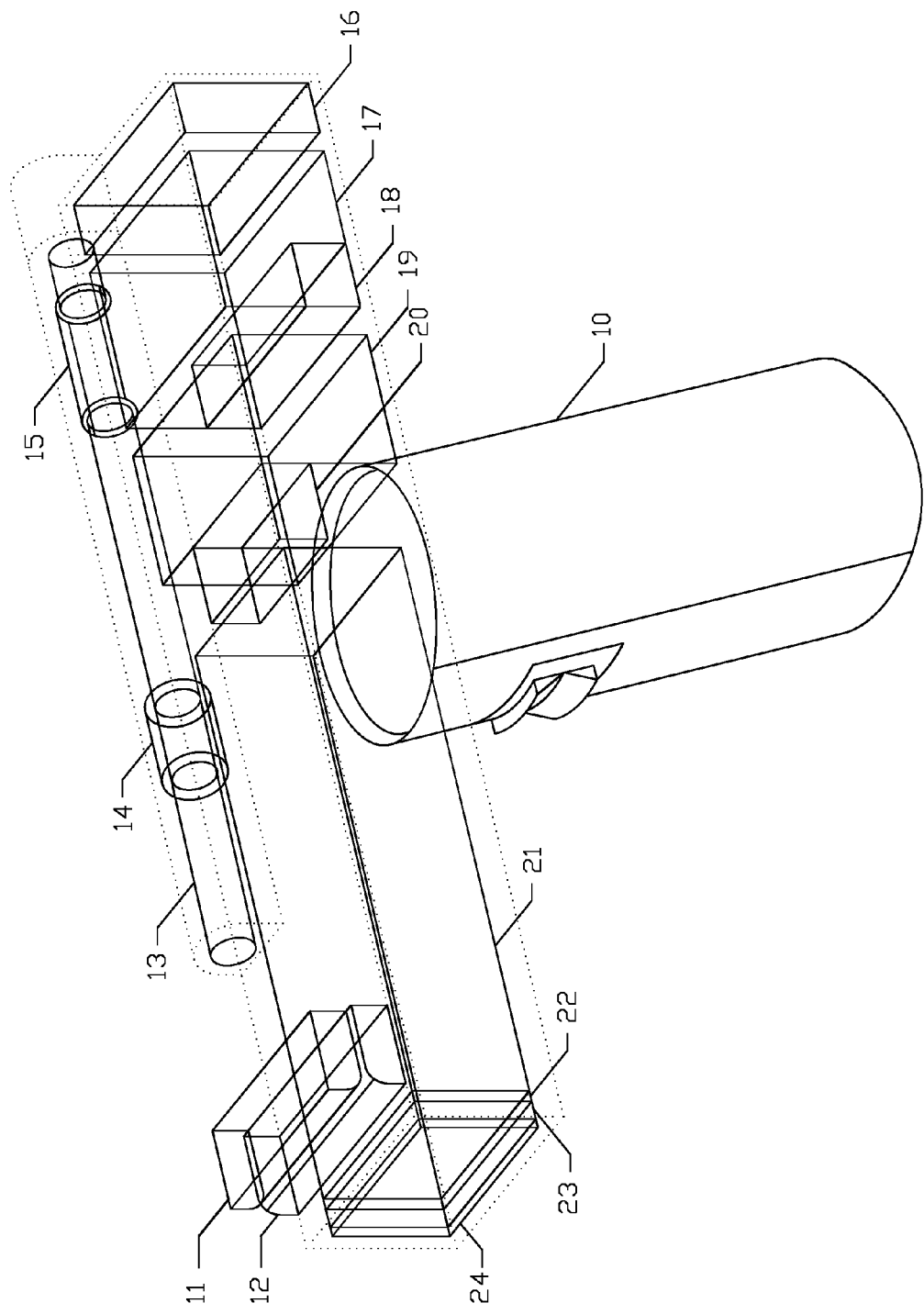
FIG. 3 shows a schematic example of individual compartments of the principal enclosure, the output shaft enclosure, the pivotable transverse parallel shaft gear assembly and the handle.

FIG. 3 shows a schematic see-through illustration of an example of individual compartments of the pivotable transverse parallel shaft gear assembly, the output shaft enclosure and the principal enclosure. Referring to FIG. 2, compartments for the pivotable transverse parallel shaft gear assembly 1 are provided in one or a plurality of configurations, including a pivotable rectangular upper gearbox 11 which is open below to a similarly configured lower gearbox 12 fixedly attached to the upper wall of the principal enclosure 3. The output shaft enclosure 5 is provided in one or a plurality of tubular configurations, which comprises an output shaft housing 13, a housing 14 for a rolling-element bearing portion of the output shaft and an output shaft gear housing 15. A bottom of the output shaft gear housing 15 is open to an upper part of the servomotor and gearbox compartment 17 to allow meshing of the output shaft gear with a gear of the gearbox. At the distal portion of the principal enclosure, there is provided a compartment 16 for an electronic control assembly behind the servomotor and gearbox compartment 17. Inside said servomotor and gearbox compartment 17, there is provided a battery compartment 18. A compartment 19 for the rack and pinion gear assembly is provided in one or a plurality of configurations, including a rectangular space bordered proximally by the rack stabilizer compartment 20 and distally by the gearbox compartment 17, which has an opening on an upper wall of said compartment for the rack to move up and down. The proximal portion of the principal enclosure 3 is provided in one or a plurality of configurations, including serially arranged rectangularly tubular compartments 22 and 24 to reversibly hold a pair of solid gel couplants to enhance ultrasound transmission between a face of the transducer and a tissue, and another rectangularly tubular compartment 23 located in between of the compartments 22 and 24 to house an electromagnetic pointing device. An ultrasound transducer is housed in a compartment 21 which is open below to a tubular space of the handle assembly 10 attached to the mid portion of the lower wall of said enclosure 3.

Figure 4:
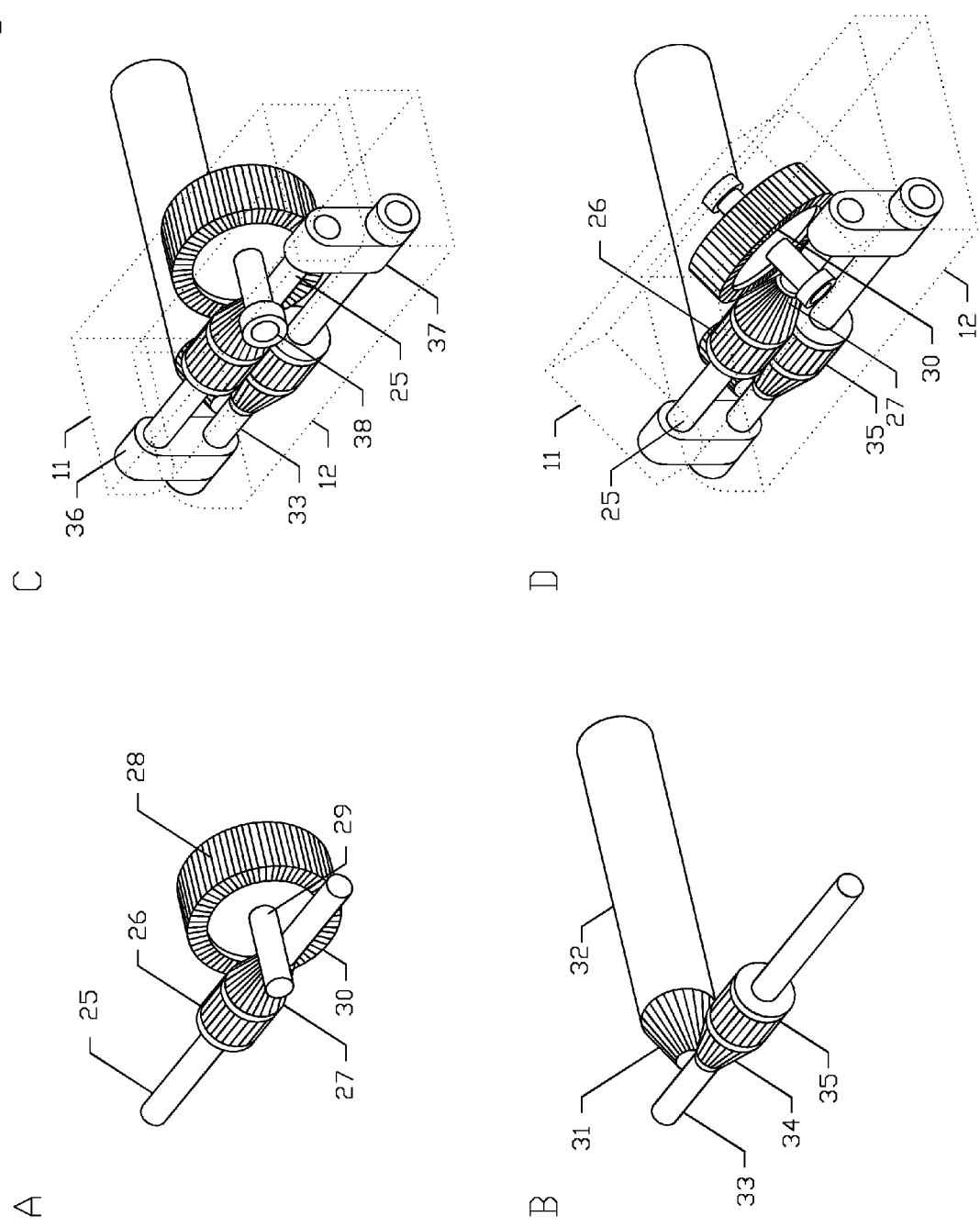
FIG. 4 shows a schematic illustration of an example of individual parts of a gear arrangement of the pivotable transverse parallel shaft gear assembly.

FIG. 4 shows a schematic illustration of an example of individual parts of a gear arrangement of the pivotable transverse parallel shaft gear assembly. Referring to FIG. 1, the pivotable transverse parallel shaft gear assembly 1 is provided in one or a plurality of configurations, including two sets of transverse shaft gears in a vertically stacked-up parallel meshing arrangement having each transverse shaft rotatably encased in a parallel shaft gear mount on each end of said shaft in a vertical configuration. As illustrated in FIG. 4A, an upper transverse parallel shaft gear assembly comprises a transverse spur gear 26 fixedly inserted over a central shaft 25, a transverse bevel gear 27 coaxially combined with said transverse spur gear 26 and a longitudinal cylindrical gear complex having a planar bevel gear 30, a cylindrical spur gear 28 on an outer cylindrical surface and a longitudinal shaft 29. The planar bevel gear 30 is projected from a plane perpendicular to the longitudinal shaft 29 of the longitudinal cylindrical gear complex. The transverse bevel gear 27 is configured to mesh at a right angle with the corresponding planar bevel gear 30. FIG. 4B shows a lower transverse shaft gear assembly which comprises a transverse spur gear 35 fixedly inserted over a central shaft 33, a transverse bevel gear 34 coaxially combined with said transverse spur gear 35 and a longitudinal bevel gear 31 located at a proximal end of the output shaft 32. The transverse bevel gear 34 is configured to mesh at a right angle with the longitudinal bevel gear 31. FIG. 4C shows the pivotable transverse parallel shaft gear assembly encased in a pair of parallel shaft gear mounts 36 and 37. Both the parallel shaft gear mounts 36 and 37 are fixedly attached to the lower gearbox 12 and maintain a vertically stacked-up meshing configuration of both the lower and upper transverse shaft gear assemblies. The parallel shaft gear mounts 36 and 37 are configured to have a rolling-element bearing joint for each end of said central shaft to reduce rotational friction of central shafts inside said shaft gear mounts. The longitudinal shaft 29 is encased in a flange which is configured to have a rolling-element bearing joint to reduce rotational friction of said shaft 29. FIG. 4D shows a pivoted upper gearbox 11 enclosing the upper transverse parallel shaft gear assembly about the central shaft 25, which maintains an unchanged parallel meshing arrangement of the spur gear 26 with the lower transverse parallel shaft spur gear 35. The meshing arrangement between the transverse bevel gear 27 and the planar bevel gear 30 remains unchanged over a range of pivoting angles.

Figure 5:
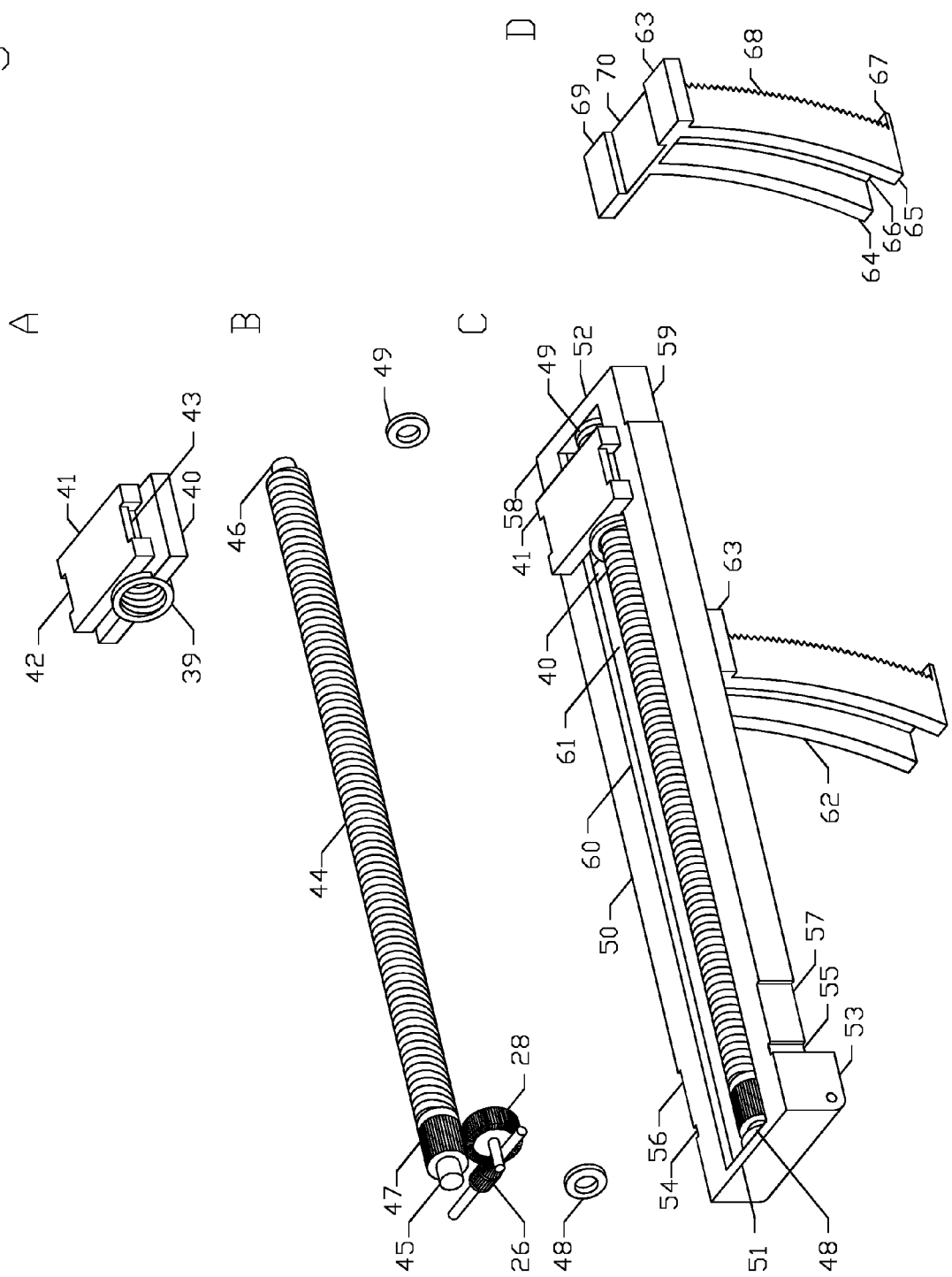
FIG. 5 shows a schematic example of individual components of the propulsion assembly.

FIG. 5 shows a schematic example of individual components of the propulsion assembly. The propulsion assembly is provided in one or a plurality of configurations including a longitudinal shaft carrying an overtube slidably moving over said longitudinal shaft. In one example, the propulsion assembly comprises a propulsion block as an overtube depicted in FIG. 5A, a longitudinal helical gear shaft in FIG. 5B and a longitudinally rectangular frame in FIG. 5C. A rack of a rack and pinion gear assembly illustrated in FIG. 5D is fixedly attached to an undersurface of a lower wall of the longitudinally rectangular frame. The propulsion block of FIG. 5A is provided in one or a plurality of configurations, which comprises a longitudinal overtube 39 having internal threads on an inner wall of said overtube, a pair of lower horizontal slide rails 40 with said each slide rail axially attached to each opposite side of an outer tubular wall of said overtube 39 and an upper slide rail 41 vertically stacked up on an upper part of said overtube 39. The upper slide rail 41 has a pair of notches 42 and 43 along longitudinal lateral edges of said slide rail 41. A longitudinal shaft limited by a proximal rotating shaft 45 and a distal rotating shaft 46 in FIG. 5B comprises a longitudinal spur gear 47 on a proximal outer surface of said shaft and a helical gear shaft 44 which has a continuous helical gear on an outer surface of said shaft between a distal end of the spur gear 47 and the distal rotating shaft 46. Both the rotating shafts 45 and 46 are encased by corresponding flanges 48 and 49 of the rectangular frame 50. The flanges 48 and 49 are configured with rolling-element bearing joint to reduce rotational friction of the rotating shafts. The outer surface of said gear shaft 44 is configured to mesh with the cylindrical spur gear 28 of the cylindrical gear complex of the upper transverse parallel shaft gear assembly of FIG. 4A.

The longitudinally rectangular frame 50 of FIG. 5C is provided in one or a plurality of configurations, which comprises an open rectangular box 60 adjoining proximal and distal portions 51 ans 52. In each inner longitudinal wall of the open rectangular box 60, a longitudinal rail slot 61 is carved, which slidably carries the lower horizontal slide rails 40 of the propulsion block 39 to and fro. The upper slide rail 41 of the propulsion block 39 slides to and fro longitudinally on an upper surface of the rectangular frame 50. The proximal portion of said frame comprises an enclosure 53 for the upper gearbox 12 of FIG. 4C and a pair of vertical notches 54 and 55 and a pair of recesses 56 and 57 on longitudinal sidewalls to releasably secure a proximal portion of the invasive tubular device assembly. The distal portion of said frame has a pair of recesses 58 and 59 on longitudinal sidewalls to releasably secure a distal portion of the invasive tubular device assembly. The rack 62 of the rack and pinion gear assembly is attached to an undersurface of a mid portion of said frame 50 via an attachment panel 63.

The rack is provided in one or a plurality of configurations including a curvilinear configuration along a vertical axis, which comprises a pair of curvilinear ridges 64 and 65 with a curvilinear recess 66 located in between of said pair of curvilinear ridges 64 and 65, a posterior leaf 67 protruding distally from a bottom of said rack, a series of gear teeth 68 protruding distally from said curvilinear ridges, a pair of attachment panels 63 and 69 and a depressed mid panel 70 located in between of said panels 63 and 69. The gear teeth 68 are configured to mesh with the pinion, which is limited by the posterior leaf 67. Circumferential size of the helical gear shaft 44 is accommodated by the depressed mid panel 70 at the attachment between said frame 50 and said rack 62.

Figure 6:
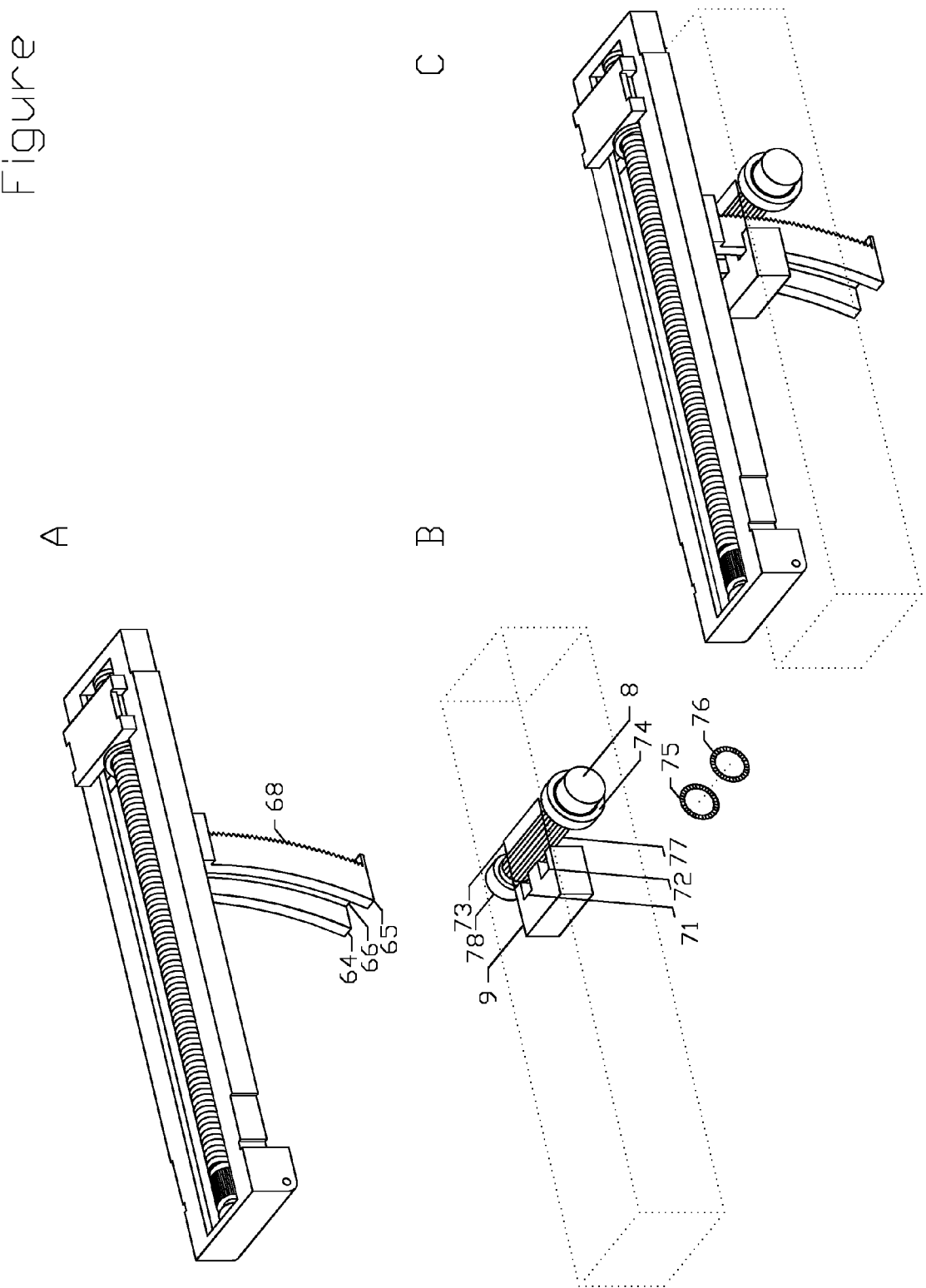
FIG. 6 shows a schematic example of arrangement of a rack and pinion gear assembly of the propulsion assembly.

FIG. 6 shows a schematic example of arrangement of individual components of the rack attached to the propulsion assembly frame with the pinion gear assembly enclosed in the principal enclosure. The pair of curvilinear ridges 64 and 65 of the rack of FIG. 6A are configured to pivotably slide up and down through a corresponding pair of curvilinear slots 71 and 72 located distally in the rack stabilizer 9 and a rectangular rack opening 73 in a mid portion of the upper wall of the principal enclosure of FIG. 9B. The gear teeth 68 of the rack mesh with the pinion 77 which is coaxially connected to the rotatable control knob 8 on one side and to a rotary position sensor 78 on the other side. The rotatable control knob 8 is provided in one or a plurality of configurations, including a double-knob configuration with an outer control knob 74, which is located outside the principal enclosure. The outer control knob 74 is configured to provide the electronic control assembly with distance information from the ultrasound transducer face to a tissue object. The rotatable control knob 8 is configured to stay immobile unless rotatably turned by an operator, by an arrangement in which the inner surface of said rotatable control knob 8 is serrated with radial threads 76 which circumferentially click with corresponding serrated radial threads 75 protruding from an outer wall of a longitudinal lateral sidewall of the principal enclosure. FIG. 6C depicts a fully arranged rack and pinion gear assembly in place.

Figure 7:
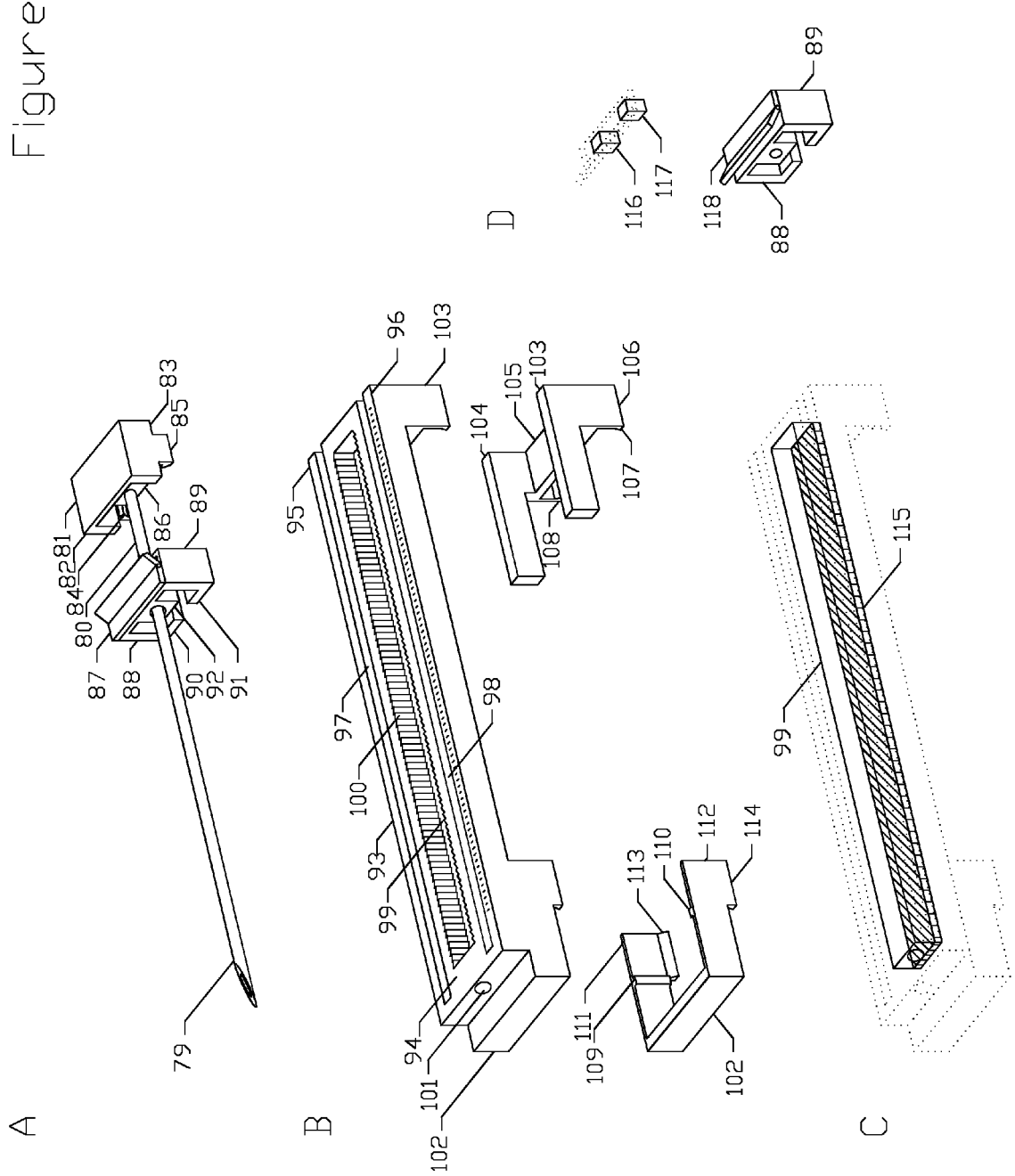
FIG. 7 illustrates a schematic example of individual components of the invasive tubular device assembly.

FIG. 7 illustrates a schematic example of individual components of the invasive tubular device assembly. An invasive tubular device assembly is provided in one or a plurality of configurations including a longitudinal invasive tubular device slidably contained in a rectangular frame. As illustrated in FIG. 7A, an example of the invasive tubular device comprises a tubular shaft 79 fixedly anchored in a distal block 81 which is configured to reversibly couple with the propulsion block 39 of FIG. 5. The distal coupling block 81 comprises a central portion 86 to anchor the distal portion of the tubular shaft 79, a pair of vertical slide rails 82 and 83 adjoining an upper part of the central portion 86 and a pair of snap-fit ridges 84 and 85 protruding downward from said vertical slide rails 82 and 83. In one example, depth of penetration of the invasive tubular device into a tissue is configured to be limited by a reversible depth lock 87 which slides over the tubular shaft 79. The depth lock 87 is provided in one or a plurality of configurations, which comprises a central portion 92 having a centrally located longitudinal tubular conduit, a pair of vertical slide rails 88 and 89 adjoining upper longitudinal side edges of the central portion and a pair of horizontal slide rails 90 and 91 inwardly projecting from a pair of lower edges of the vertical slide rails 88 and 89, respectively. As illustrated in FIG. 7D, a rocker-switch-type lock and release lever 118 of the depth lock 87 is transversely attached on an upper surface of the central portion, which has a pair of protuberances 116 and 117 fixedly attached to an undersurface of a distal part of said lock and release lever 118.

The rectangular frame 93 is provided in one or a plurality of configurations including one example depicted in FIG. 7B, which comprises a protective open box shell 99 to hold said invasive tubular device inside said shell 99, a pair of longitudinal rail guides 95 and 96 on a pair of corresponding longitudinal sidewalls of said open box shell 99 to form a pair of longitudinal rail slots 97 and 98 in between of said rail guide and said sidewall to carry both the coupling block 81 and depth lock 87, a serrated inner surface 100 of each inner longitudinal sidewall of said open box shell 99 for reversible fastening of the depth lock 87 and a tubular conduit 101 in a proximal portion of said rectangular frame 93 for passage of the invasive tubular device toward a tissue object. The longitudinal rail slots 97 and 98 allow vertical slide rails 82 and 83 of the distal coupling block and vertical slide rails 88 and 89 of the depth lock to slide in and out of of said invasive tubular device assembly along the longitudinal axis. On an upper surface of one of the longitudinal rail guides, there is provided a series of distance markings to help measure length of the invasive tubular device in a tissue. The protuberances 116 and 117 of the lock and release lever 118 are configured to exert an outward pressure on serrated inner longitudinal sidewalls when lowered into the open box shell 99, thereby reversibly locking the depth lock 87 in place. Raising back the protuberances 116 and 117 by a reverse position of the lock and release lever 118 removes the outward pressure, which unlocks the depth lock 87 from the open box shell 99. A pair of lateral sidewalls 111 and 112 of a proximal portion 102 of the rectangular frame 93 have a set of snap-fit vertical ridges 109 and 110 and horizontal ridges 113 and 114 protruding downward to be releasably inserted into corresponding snap-fit notches of the propulsion assembly shown in FIG. 5C. Similarly, distal rail guides 103 and 104 have horizontal snap-fit ridges 107 and 108, respectively, protruding downward to be slidably inserted to corresponding snap-fit notches of the propulsion assembly shown in FIG. 5C. For an illustration, the horizontal snap-fit ridge 107 is shown to be connected to the rail guide 103 via a lateral guide wall 106. The distal rail guides 103 and 104 are connected to each other by a transverse planar bridge 105 under the open box shell but are not connected to a transverse sidewall of the distal end of said invasive tubular device assembly, which allows the invasive tubular device to be releasably removable through the open distal end of said invasive tubular device assembly. As schematically illustrated in FIG. 7C, the open box shell 99 is configured with an open upper portion and a closed bottom wall 115, which allows biologic materials associated with the invasive tubular device to be contained in said box shell 99.

Figure 8:
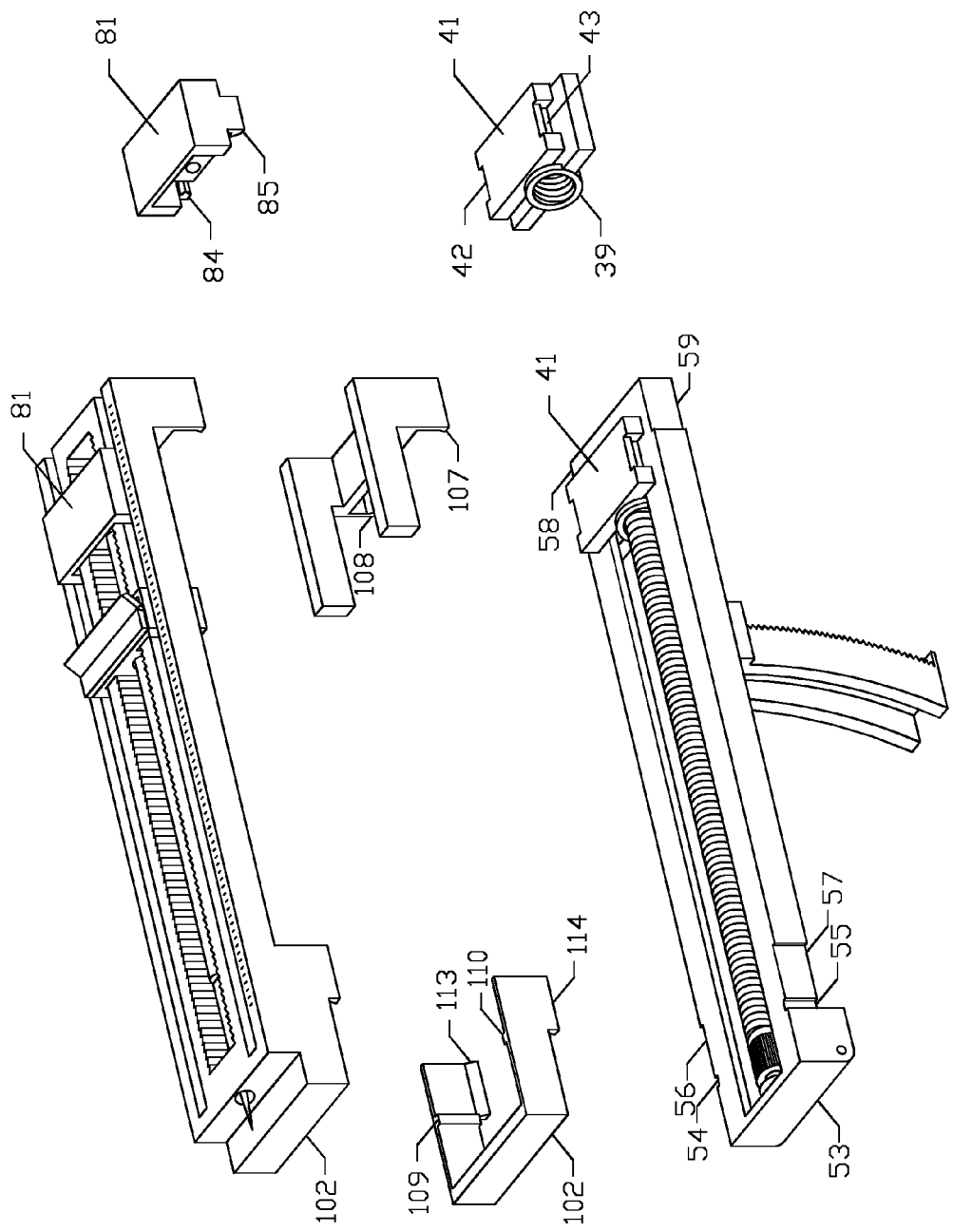
FIG. 8 depicts a schematic example of a reversible snap-fit coupling between the invasive tubular device assembly and the propulsion assembly.

FIG. 8 illustrates a schematic example of a reversible snap-fit coupling between the invasive tubular device assembly and the propulsion assembly. At the proximal portion 102 of the invasive tubular device assembly, two vertical ridges 109 and 110 are reversibly insertable in corresponding vertical notches 54 and 55 of the propulsion assembly, which is configured to prevent forward slipping of the invasive tubular device assembly. Two horizontal ridges 113 and 114 reversibly fasten corresponding horizontal lower edges of lateral recesses 56 and 57 of the propulsion assembly by snap-fit coupling, which is configured to prevent vertical separation of said proximal portion of said invasive tubular device assembly from said propulsion assembly. Similarly, two horizontal ridges 107 and 108 of the distal portion of the invasive device assembly are configured to get reversible snap-fit fastening below corresponding horizontal lower edges of lateral recesses 58 and 59 of the propulsion assembly. The pair of ridges 84 and 85 of the distal coupling block 81 of the invasive tubular device assembly reversibly fasten corresponding horizontal notches 42 and 43 of the upper slide rail 41 of the propulsion block 39 by snap-fit coupling, which is configured to prevent both longitudinal and vertical separation of said distal coupling block from said propulsion block.

Figure 9:
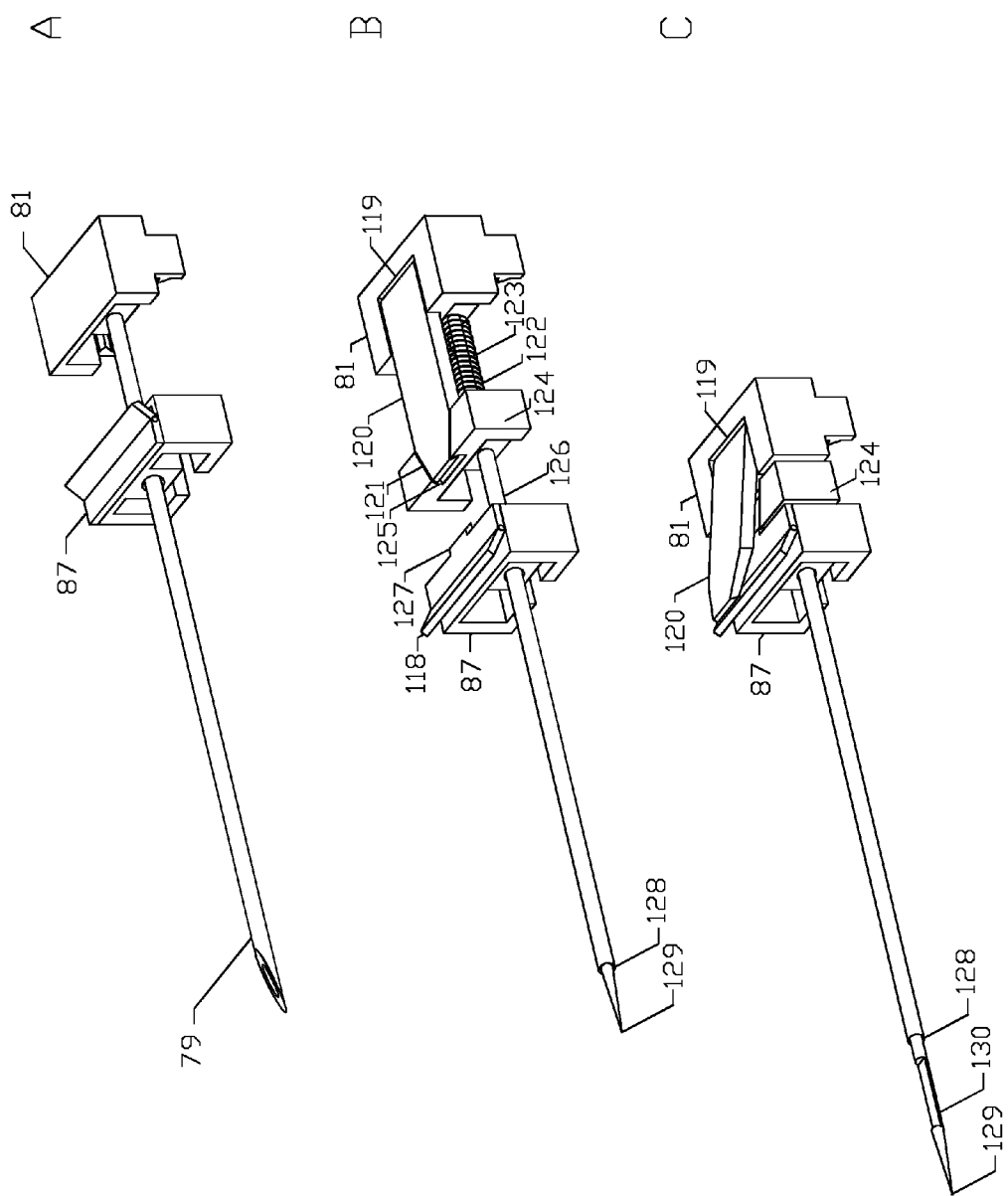
FIG. 9 shows a schematic example of invasive tubular devices and an actuator mechanism for firing an inner stylet.

As schematically illustrated in FIG. 9, an invasive tubular device is provided in one or a plurality of configurations including the tubular shaft 79 fixedly anchored in the distal coupling block 81 and the depth lock 87 slidably placed over said tubular shaft 79. In other example shown in FIGS. 9B and 9C, the invasive tubular shaft comprises an outer tubular shaft 126, an inner stylet 123 to procure tissue samples and an actuator mechanism to advance the inner stylet to procure tissue samples. The stylet 123 may have a biopsy sample notch 130 near a proximal end 129 of said stylet, which is configured to capture a tissue sample by a linear movement of said stylet inside the tubular shaft of the invasive tubular device. Both the coupling block 81 and depth lock 87 of the invasive tubular device have a concerted actuator mechanism for the stylet to be fired toward a tissue object, which comprises a tandem arrangement of two-part blocks 81 and 124, with each separated by a pivotable separator panel 120, and the depth block 87 having a transverse ridge 127 from a distal transverse edge of a lock and release lever 118. The distal coupling block 81 fixedly anchors a distal portion of the stylet 123 and a distal portion of a compression spring 122, and has a rectangular separator panel slot 119 longitudinally carved in an upper surface of the central portion. The pivotable separator panel 120 is pivotable on a transverse axis provided in a distal portion of said separator panel slot 119. A second part 124 of the two-part coupling block is located proximally to the distal coupling block 81 and fixedly anchors a distal portion of the outer tubular shaft 126 proximally and the compression spring 122 distally. The second part 124 has a flat trapezoidal slot 121 carved in an upper surface of said second part, with which a proximal portion of the pivotable separator panel 120 is insertably and reversibly coupled in a snap-fit coupling. A proximal transverse edge of the pivotable separator has a transverse notch 125 on a lower half, which is configured to let the transverse ridge 127 inserted into said notch and lift up said proximal transverse edge. Sequence of actuation of the stylet 123 for obtaining tissue samples starts with the two-part coupling block 81 and 124 separated by the pivotable separator panel 120 moving toward the depth lock 87 in a locked position, driven by the propulsion block 39 of FIG. 8. When a proximal end of the second part 124 touches a distal end of the depth lock 87, the transverse ridge 127 dislodges the pivotable separator panel 120 from the trapezoidal slot 121. The proximal portion of the pivotable separator panel 120 is lifted up and the two-part coupling block 81 and 124 and the depth block 87 get all stacked up longitudinally along the axis, with a proximal end of said coupling block 81 driven to a distal end of the second part 124 compressing the compression spring 122. The biopsy sample notch 130 protrudes from a tip 128 of the tubular shaft 126. The propulsion block 39 then retracts the distal coupling block 81, which helps a tissue sample procured in the tubular shaft 126. The compression spring 122 pushes the distal coupling block 81 distally during retraction in a way said second part 124 stays abutting the distal end of the depth block 87, thereby maintaining a steady position of the tubular shaft in the tissue while the stylet 123 is being retracted.

FIG. 10 shows a schematic illustrative example of angulation of the propulsion assembly relative to the principal enclosure. FIG. 10A shows a parallel configuration of the propulsion assembly with the principal enclosure along a longitudinal axis of the apparatus. The helical gear shaft 44 is longitudinally enclosed in the rectangular frame 50 of the propulsion assembly, which proximally meshes with the cylindrical spur gear 28 of the pivotable transverse shaft gear assembly comprising the upper transverse shaft spur gear 26 meshing with the lower transverse shaft spur gear 35. A series of gear teeth 68 of the rack meshes with the pinion 77 which is controllably rotatable by the rotatable control knob 8. As depicted in FIG. 10B, the rotatable control knob 8 rotates the pinion 77 which rotates the gear teeth 68 of the rack, which pivots the upper transverse shaft spur gear 26 to an angle of the propulsion assembly relative to a horizontal axis of a ultrasound transducer face enclosed in the proximal open window portion 2 of the principal enclosure 3. Range of angulation is configured to be limited by the posterior leaf 67 which restricts further rotational movement of the gear teeth 68 by the pinion 77.

Figure 11:
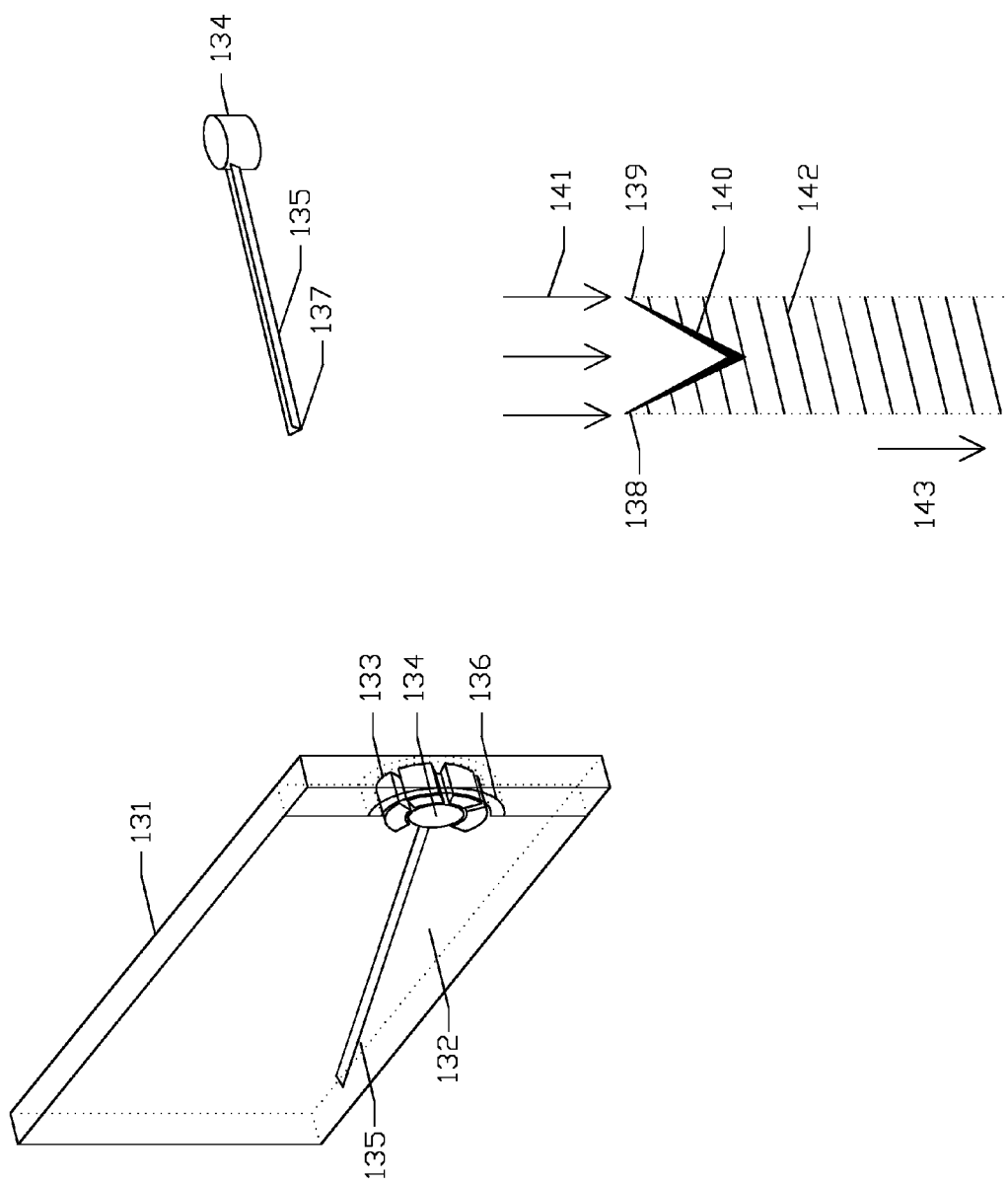
FIG. 11 shows a schematic illustration of an example of a galvanometer-type electromagnetic pointing device.

FIG. 11 shows a schematic illustration of an example of a galvanometer-type electromagnetic pointing device, provided in one or a plurality of electromechanical configurations, which comprises a substantially ultrasound-transparent flat rectangular box 131 and an electromagnetic pointing device 133~135. The flat rectangular box 131, provided in one or a plurality of configurations, is located proximal to the face of the transducer, which is made of substantially ultrasound-transparent polymer(s), filled with one or a plurality of type(s) of substantially ultrasound-transparent liquid and leak-proof. The substantially ultrasound-transparent liquid is electrically non-conductive. The galvanometer-type electromagnetic pointing device uses varying range of electric voltage, current or resistance to radially move a linear movable pointer 135 around a center of said device. The linear movable pointer 135 is configured to protrude into a space 132 in the flat rectangular box 131, to move inside said flat rectangular box from side to side and to block ultrasound transmission at a right angle, which is visualized in an ultrasonographic view. The galvanometer-type device comprises a U-shaped set of electromagnetic windings 133 circumferentially surrounding a pivoting wire core 134 and the linear movable pointer 135 connected to the pivoting wire core 134. A semicircular wall 136 immobilizes the windings 133 in a U-shaped configuration. Both the pivoting wire core 134 and the windings 133 are electrically connected to the power and electronic control assembly. All components of the galvanometer-type electromagnetic pointing device are configured as waterproof. Both proximal and distal surfaces of the flat rectangular box contact with a pair of gel couplants to enhance ultrasound transmission. The linear movable pointer 135 is provided in one or a plurality of configurations to enhance blockade of transmissible ultrasonographic waves across said movable pointer, including a V-shaped cross-sectional configuration. In this example, a tip 137 of the linear movable pointer and a cross-sectional view 140 are V-shaped, with an inner surface of the V facing incident ultrasonographic waves 141. The V-shaped cross-section of the linear movable pointer is to reduce obtuse diffusion of rebounded ultrasound waves from the linear movable pointer. A post-acoustic shadow 142 to a direction 143 toward a tissue is limited by a pair of sharp-edged borders of 138 and 139.

Figure 12:
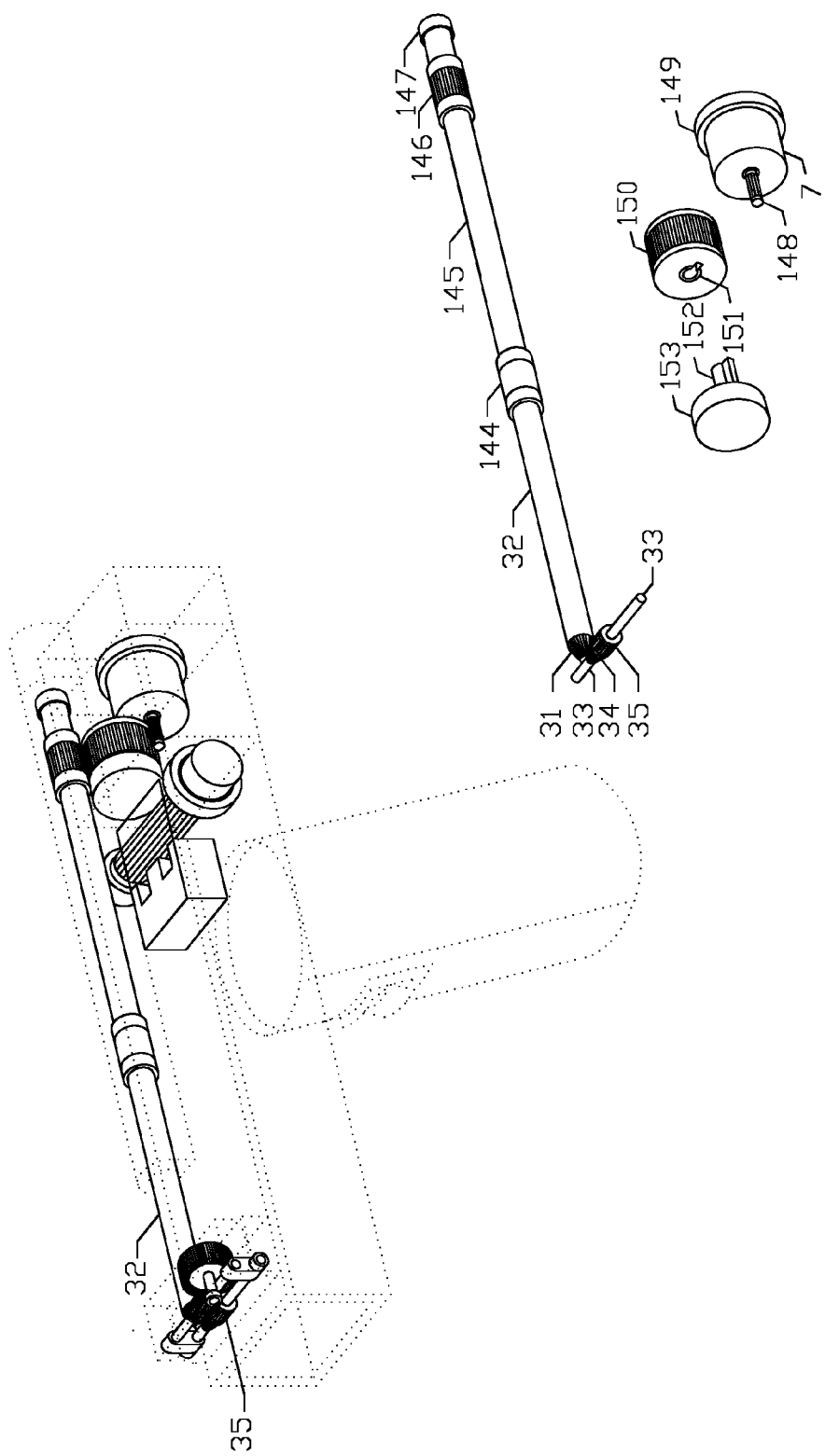
FIG. 12 shows a schematic example of a servomotor and gearbox assembly which is connected to the pivotable transverse parallel shaft gear assembly.

FIG. 12 shows a schematic example of a servomotor and gearbox assembly, provided in one or a plurality of configurations including a parallel spur gear arrangement, which comprises an electric servomotor 7, a pair of spur gears 146 and 150, and a multi-turn rotary position sensing device 153 such as potentiometer, optical encoder or magnetic encoder. The electric servomotor 7 is irreversibly fastened by a flange 149 to a distal wall of said servomotor and gearbox assembly, with its rotor 148 protruding longitudinally along the axis. A protruded portion of the rotor 148 is configured as a longitudinal spur gear that meshes in parallel with the cylindrical spur gear 150. The cylindrical spur gear 150 is connected coaxially to the rotary position sensor 153 by coupling of a central rotatable rod 152 of said rotary position sensor with a central tubular space 151 of said spur gear. The rotary position sensor 153 is fastened to a proximal wall of said servomotor and gearbox assembly. The multi-turn rotary position sensor 153 measures rotational displacements of said cylindrical spur gear 150 and is electronically connected to the power and electronic control assembly that receives an electronic information from said rotary position sensor of a rotational displacement of the cylindrical spur gear 150 to calculate a longitudinal displacement of the propulsion block 39 slidably over the helical gear shaft 44 of the propulsion assembly of FIG. 5. The cylindrical spur gear 150 meshes with another longitudinal spur gear 146 that merges with an output shaft 145 located inside the output shaft enclosure. Portions of the output shaft 145 inside the output shaft enclosure are configured to reduce rotational friction between the output shaft and the output shaft enclosure, which comprise a rolling-element bearing portion 144 and a rolling-element bearing joint flange 147 at a distal end encircling said output shaft. The output shaft inside the output shaft enclosure merges with a portion 32 outside said enclosure which then merges with the bevel gear 31 of the pivotable transverse shaft gear assembly at a proximal end.

Figure 13:
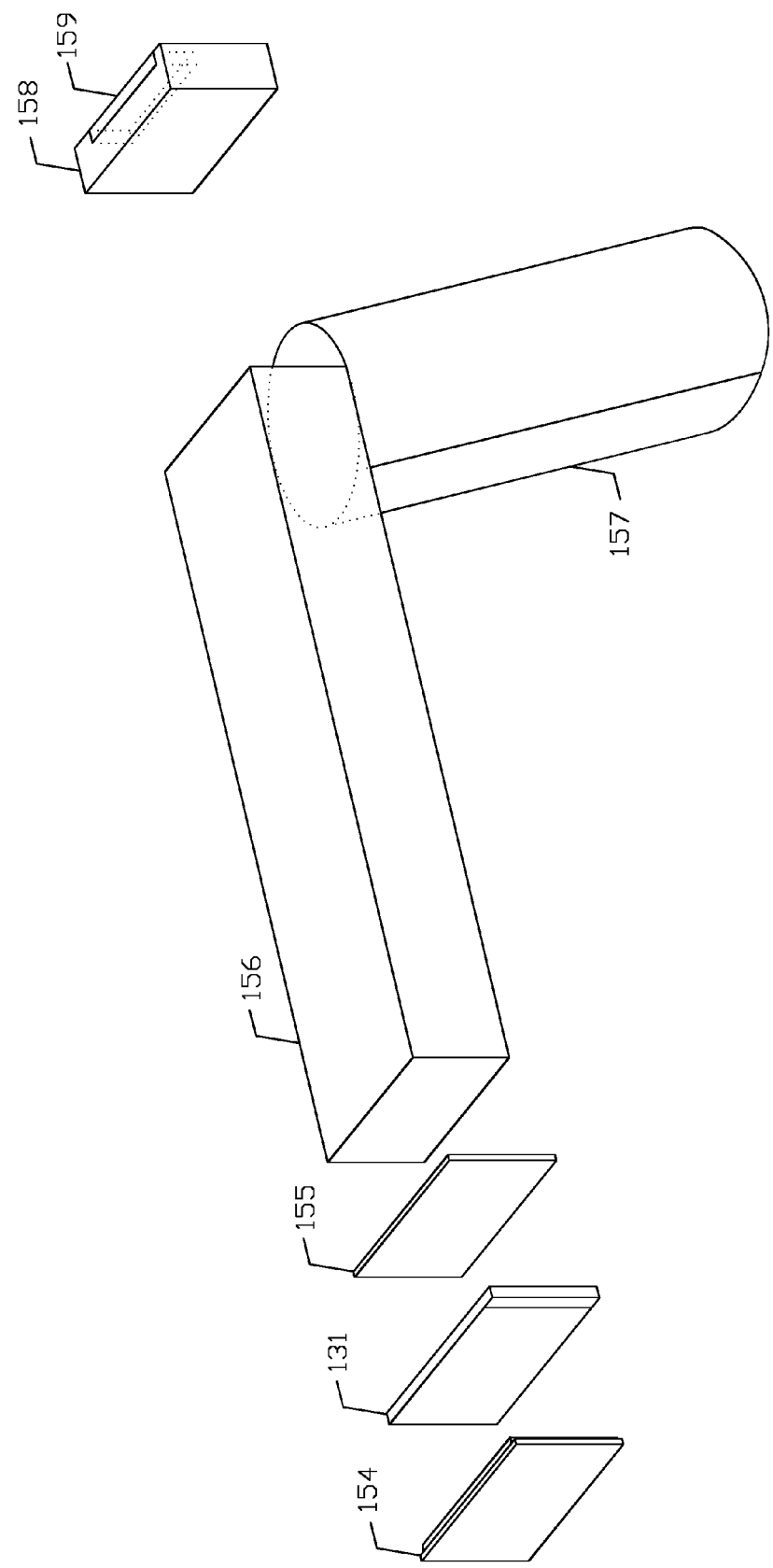
FIG. 13 depicts a schematic illustration of components housed in the principal enclosure.

FIG. 13 depicts a schematic illustration of components housed in the principal enclosure. A non-reusable solid gel couplant 154 slidably is placed in front of the electromagnetic pointing device 131 and a second solid gel couplant 155 is placed in between of said electromagnetic pointing device 131 and an ultrasound transducer 156. The solid gel couplant 154 contacts with a skin overlying a tissue object. The transducer 156 is configured to be electrically connected to a main ultrasonographic machine through electric cables housed in a handle portion 157 attached to a bottom of said transducer. The electronic control assembly 158 having an integrated circuit board with a segment digital display 76 is placed in the distal portion of the positioning guide control assembly. The segment digital display 159 is configured to be seen through the distal wall of said principal enclosure.

FIG. 14 depicts a schematic illustration of an example of a method of coordination of an angular rotation of the invasive tubular device frame 93 together with the propulsion assembly with a horizontal movement of the linear movable pointer 160 of the positioning assembly to aim at a tissue object 162. The positioning assembly is configured to coordinate angulation of the invasive tubular device frame 93 with horizontal movement of the linear movable pointer 160 in ways to have a longitudinal axis of the invasive tubular device frame 93 cross a linear shadow 161 at the tissue object. In FIGS. 14A, 14B and 14C, upper drawings represent a schematic top-down view of the electromagnetic pointing device showing the linear movable pointer 160 radially moving. Mid drawings show a schematic profile view of the apparatus placed atop a skin overlying the tissue object 162. Lower drawings depict a schematic ultrasonographic two-dimensional view 163 seen in a monitor of an ultrasonographic machine. As illustrated in FIG. 14A, once the apparatus is placed on the skin above the tissue object 162, the linear movable pointer 160 generates a linear shadow 161 in the two-dimensional view 163 by blocking off transmissible ultrasonographic waves. In this example, the linear shadow 161 is seen away in a distance from an ultrasonographic image 163 of the tissue object 164. In FIG. 14B, based on a vertical distance 168 from the transducer face to the tissue object 162, the invasive tubular device frame 93 is rotated about a pivoting center 165 to an angle 167, enabling a longitudinal axis 166 of said invasive tubular device frame 93 to cross the tissue object 162. The rotation of said invasive tubular device frame 93 by manually rotating the pinion of the rack and pinion assembly of FIG. 10 electronically translates into a horizontal movement of the linear movable pointer 160 to a position vertically linear up from the tissue object 162, which is monitored real-time in the two-dimensional ultrasonographic view 163. A crossing of the linear shadow 160 through the tissue object 162 indicates a crossing of the longitudinal axis 166 of the invasive tubular device frame 93 through said tissue object 162. FIG. 14C shows an example of a more acute angle 169 of the invasive tubular device frame 93 calculated from a shorter vertical distance 170 between the tissue object 162 and the transducer face while the linear shadow 161 moves the same distance as in FIG. 14B, illustrating an effect of vertical distance between the ultrasound transducer face and the tissue object on angulation of the invasive tubular device frame.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. An automated stereotactic apparatus for tissue sampling under ultrasonographic guidance, comprising:

an invasive tubular device assembly, guided by a positioning assembly and propelled by a powered propulsion assembly;

the invasive tubular device assembly, provided as a non-reusable hand-held operating device comprising an invasive tubular device frame having a longitudinal rail guide on each sidewall of said invasive tubular device frame and an invasive tubular device, wherein said invasive tubular device frame is configured to slidably house the invasive tubular device inside said invasive tubular device frame, and wherein said invasive tubular device is reversibly coupleable with the powered propulsion assembly so as to axially move along said longitudinal rail guide of said invasive tubular device frame;

the positioning assembly, provided as a hand-held operating device comprising a position alignment assembly and a positioning control assembly, wherein said position alignment assembly is configured to movably block a portion of ultrasonographic waves to produce an ultrasonographically visible linear shadow line in an ultrasonographic display, wherein said positioning control assembly is reversibly coupleable with the invasive tubular device assembly, and wherein said positioning control assembly is configured to synchronize axial rotation of said positioning control assembly with movable blockade of the portion of the ultrasonographic waves in the ultrasonographic display; and the powered propulsion assembly, provided as a hand-held operating device comprising a transmission assembly having a pivotable gearbox and an electric motor device, wherein said powered propulsion assembly is reversibly coupleable with the invasive tubular device assembly, wherein said pivotable gearbox is configured to pivot said powered propulsion assembly thereof at a proximal end of said powered propulsion assembly, and wherein a rotational power generated by the electric motor device is configured to be transmitted to the invasive tubular device assembly over a pivoting range of said proximal end of said powered propulsion assembly.

2. The automated stereotactic apparatus for tissue sampling under ultrasonographic guidance according to claim 1, wherein the invasive tubular device assembly further comprises:

the invasive tubular device, comprising a tubular shaft with a stylet slidably placed inside said tubular shaft, a tandem two-part coupling device with a first part fixedly attached to a distal end of the stylet located distally to a second part fixedly attached to a distal end of the tubular shaft and a depth lock device detachably placed over the tubular shaft, wherein a proximal portion of said invasive tubular device is configured to penetrate tissue and procure a tissue sample, wherein the first part of the coupling device attached to the stylet is configured to reversibly couple with the powered propulsion assembly, wherein the depth lock device is configured to variably limit a penetration length of said invasive tubular device into the tissue, wherein said invasive tubular device is configured to axially slide in the invasive tubular device frame, and wherein said invasive tubular device is configured to controllably penetrate the tissue over a range of the angle of insertion; and the invasive tubular device frame, comprising an open box shell having an open upper portion and a closed bottom wall, the longitudinal rail guide on each longitudinal sidewall of the open box shell, a serrated inner surface of the each longitudinal sidewall, and a plurality of snap-fit ridges disposed on a lower surface of proximal and distal ends of said invasive tubular device frame, wherein said longitudinal rail guide and the each longitudinal sidewall are configured to form a rail slot to axially move the invasive tubular device, wherein said serrated inner surface of the each longitudinal sidewall is configured to limit an axial movement of the invasive tubular device, wherein said invasive tubular device frame is configured to reversibly couple with the powered propulsion assembly, wherein said invasive tubular device frame is configured to hold biologic materials from the invasive tubular device, and wherein said invasive tubular device frame is configured to let a proximal portion of the invasive tubular device move in and out of an aperture disposed in a proximal wall of said invasive tubular device frame.

3. The automated stereotactic apparatus for tissue sampling under ultrasonographic guidance according to claim 2, wherein the invasive tubular device further comprises a compression spring coaxially located in between the first part and the second part of the tandem two-part coupling device and a pivotable separator panel disposed on an upper portion of said first part;

wherein said compression spring is inserted over the tubular shaft and fixedly attached to an outer portion of a distal wall of said second part and an outer portion of a proximal wall of said first part of said tandem two-part coupling device;

wherein said compression spring is configured to be compressed by a forward movement of said first part toward said second part and to extend back by a backward movement of said first part away from said second part, whereby the stylet attached to said first part is coaxially pulled back through the tubular shaft attached to said second part of said tandem two-part coupling device;

wherein, in a pre-firing position of the stylet into the tissue object, said pivotable separator panel is configured to be releasably locked into a pivotable separator panel slot disposed on an upper portion of said second part of said tandem two-part coupling device, whereby said second part is separated from said first part of said tandem two-part coupling device and a proximal portion of the stylet is pulled inside the tubular shaft;

wherein a proximal part of said pivotable separator panel is configured to be lifted up about a pivot of said pivotable separator panel attached to said upper portion of said first part of said tandem two-part coupling device by a contact with a transverse ridge protruding distally from an upper panel of the depth lock device of said invasive tubular device, whereby said first part moves toward said second part of said tandem two-part coupling device and the stylet advances into the tissue object; and wherein said first part of said tandem two-part coupling device is configured to couple with and to be driven by the linear propulsion device of the powered propulsion assembly.

4. The automated stereotactic apparatus for tissue sampling under ultrasonographic guidance according to claim 1, wherein the positioning assembly further comprises:

the position alignment assembly, comprising an electromagnetic pointing assembly and a first electronic position sensing device, wherein said electromagnetic pointing assembly is located in front of an ultrasound transducer and is configured to movably block the portion of ultrasonographic waves so as to generate the ultrasonographically visible linear shadow in the ultrasonographic display, wherein said first electronic position sensing device is mechanically attached to and is configured to monitor position changes in said positioning control assembly, wherein said electromagnetic pointing assembly and said first electronic position sensing device are electrically connected to and controlled by a power and electronic control assembly, wherein said first electronic position sensing device is configured to provide said power and electronic control assembly with a rotational position information of said positioning control assembly, wherein said position alignment assembly is configured to provide an ultrasonographic position information of the tissue object in relation to a position of the ultrasound transducer placed over the tissue object, and wherein said position alignment assembly is configured to align the longitudinal axis of the invasive tubular device with said tissue object;

the positioning control assembly, comprising a rack and pinion gear assembly disposed distally to the ultrasound transducer, wherein a pinion of said rack and pinion gear assembly is coaxially attached to the first electronic position sensing device, wherein a rack of said rack and pinion gear assembly is fixedly attached to a part of the powered propulsion assembly, wherein said positioning control assembly is configured to pivot the invasive tubular device assembly reversibly attached to the powered propulsion assembly about a proximal portion of said powered propulsion assembly, and wherein said positioning control assembly is configured to controllably angulate the invasive tubular device slidably disposed in the invasive tubular device assembly attached to the powered propulsion assembly so as to make said invasive tubular device reach the tissue object at an angle;

an ultrasound transducer enclosure, provided in a tubular configuration, wherein said ultrasound transducer enclosure is configured to house the ultrasound transducer, and wherein said ultrasound transducer enclosure is configured to align longitudinal and horizontal axes of said ultrasound transducer enclosure with longitudinal and horizontal axes of the ultrasound transducer, respectively; and a handle, provided in a tubular configuration, wherein said handle is configured to be connected to a lower wall of the ultrasound transducer enclosure, wherein said handle is configured to serve as a conduit for electric cables between the ultrasound transducer and a main ultrasonographic machine, and wherein said handle comprises an electric switch electrically configured to control the powered propulsion assembly.

5. The automated stereotactic apparatus for tissue sampling under ultrasonographic guidance according to claim 4, wherein the electromagnetic pointing assembly of the position alignment assembly comprises a substantially ultrasound-transparent flat box and a galvanometer electromagnetic pointing device and a pair of gel couplants;

wherein said substantially ultrasound-transparent flat box is configured to house said galvanometer electromagnetic pointing device;

wherein said substantially ultrasound-transparent flat box is configured to be leak-proof and is filled with an electrically non-conductive liquid;

wherein said substantially ultrasound-transparent flat box is located in front of the ultrasound transducer;

wherein said galvanometer electromagnetic pointing device comprises a linear movable pointer attached to an electromagnetic moving coil unit;

wherein said galvanometer electromagnetic pointing device is configured to use electric voltage, current or resistance provided by the power and electronic control assembly;

wherein components of said galvanometer electromagnetic pointing device are waterproof;

wherein said linear movable pointer is configured to block transmissible ultrasound waves across said linear movable pointer; and wherein a first gel couplant is placed in between said ultrasound transducer and said substantially ultrasound-transparent flat box and a second gel couplant is placed in front of said substantially ultrasound-transparent flat box.

6. The automated stereotactic apparatus for tissue sampling under ultrasonographic guidance according to claim 4, wherein the positioning control assembly further comprises a rotatable control knob coaxially attached to the pinion gear of the rack and pinion gear assembly;

wherein said rotatable control knob is provided in a coaxial double-knob configuration having an outer rotatable control knob and an inner rotatable control knob and is operable by an operator;

wherein said outer rotatable control knob is configured to provide the power and electronic control assembly with a numerical information of a distance between the ultrasound transducer and the tissue object; and wherein said inner rotatable control knob is configured to rotate said pinion gear which meshes with the rack of said rack and pinion gear assembly.

7. The automated stereotactic apparatus for tissue sampling under ultrasonographic guidance according to claim 1, wherein the powered propulsion assembly further comprises:

the electric motor device, located distally to the positioning control assembly, comprising an electric motor, a cylindrical spur gear fixedly connected to a rotor of said electric motor, and a second electronic position sensing device coaxially attached to a rotatable central rod of said cylindrical spur gear, wherein said electric motor device is configured to generate and transmit the rotational power from said electric motor to the transmission assembly, wherein said cylindrical spur gear of said electric motor device is configured to mesh with a gear of the transmission assembly, wherein the second electronic position sensing device is configured to measure rotational displacement of said cylindrical spur gear of said electric motor device, and wherein said electric motor device is connected to and controllably powered by the power and electronic control assembly;

the transmission assembly, comprising a spur gearbox located distally to the positioning control assembly, a longitudinal output shaft gear located outside the ultrasound transducer enclosure, and the pivotable gearbox located outside the ultrasound transducer enclosure thereof at a proximal end of said ultrasound transducer enclosure, wherein said spur gearbox is configured to deliver the rotational power from the electric motor to said longitudinal output shaft gear by (1) meshing with the cylindrical spur gear of the electric motor device and by (2) meshing with said longitudinal output shaft gear thereof at a distal end of said longitudinal output shaft gear, wherein said longitudinal output shaft gear is configured to transmit said rotational power to said pivotable gearbox by meshing with a transverse bevel gear of said pivotable gearbox, wherein said pivotable gearbox comprises two transverse shaft gear devices arranged in parallel, with a first transverse shaft gear device having a vertical meshing arrangement with a second transverse shaft gear device, and wherein said second transverse shaft gear device is configured to pivot about a rotatable center of said second transverse shaft gear device over a range of an angle between said first and second transverse shaft gear devices while maintaining said vertical meshing arrangement with said first transverse shaft gear device;

a linear propulsion gearbox assembly, comprising a longitudinal rotatable gear shaft axially placed in the linear propulsion gearbox frame and a linear propulsion device inserted over said longitudinal rotatable gear shaft, wherein said longitudinal rotatable gear shaft comprises a longitudinal spur gear at a proximal end of said longitudinal rotatable gear shaft proximal to a helical gear, wherein said linear propulsion device comprises an overtube with internal helical threads on an inner surface of said overtube and a horizontal slide rail fixedly attached to each side of said overtube, wherein said longitudinal spur gear of said longitudinal rotatable gear shaft is configured to mesh with a gear of the pivotable gearbox of the transmission assembly, wherein said helical gear of said longitudinal rotatable gear shaft is configured to mesh with said internal helical threads of said linear propulsion device, wherein said horizontal rail of said linear propulsion device is configured to slide in a longitudinal rail slot of the linear propulsion gearbox frame, wherein said linear propulsion device is configured to couple with the first part of the coupling device of the invasive tubular device, and wherein said linear propulsion device is configured to move along a longitudinal axis of the linear propulsion gearbox frame; and a linear propulsion gearbox frame, comprising an open box shell having open upper and lower portions, the longitudinal rail slot on an inner surface of each longitudinal sidewall of said open box shell, and an inner central rod protruding from an inner surface of proximal and distal walls, wherein said inner central rod of said linear propulsion gearbox frame is configured to rotatably anchor the longitudinal rotatable gear shaft, wherein said longitudinal rail slot of said linear propulsion gearbox frame is configured to slidably mate with the horizontal rail of the linear propulsion device, wherein a part of an undersurface of said open box shell of said linear propulsion gearbox is configured to be fixedly attached to an upper part of the rack of the rack and pinion gear assembly of the positioning control assembly, and wherein said linear propulsion gearbox frame is configured to reversibly couple with the invasive tubular device assembly.

8. The automated stereotactic apparatus for tissue sampling under ultrasonographic guidance according to claim 7, wherein each transverse shaft gear device of the pivotable gearbox of the transmission assembly further comprises a transverse spur gear fixedly inserted over a central shaft, a transverse bevel gear coaxially adjoining said transverse spur gear;

wherein each shaft end of said transverse shaft gear device is rotatably inserted in an aperture of a transverse shaft gear mount;

wherein an apex of the transverse bevel gear of the first transverse shaft gear device is configured to be in an opposite direction to an apex of the transverse bevel gear of the second transverse shaft gear device;

wherein the transverse spur gear of the first transverse shaft gear device is configured to mesh with the transverse spur gear of the second transverse shaft gear device in the vertical meshing arrangement with said second transverse shaft gear device located vertically above said first transverse shaft gear device;

wherein said second transverse shaft gear device is configured to mesh at a right angle with a planar bevel gear disposed on a proximal surface of a cylindrical gear; and wherein said second transverse shaft gear device and said cylindrical gear having said planar bevel gear meshing with said second transverse shaft gear device is pivotable about said aperture of said transverse shaft gear mount which said shaft end of said second transverse shaft gear device is inserted in.

9. A method of tissue sampling under ultrasonographic guidance, comprising;

providing an automated stereotactic apparatus of claim 1;

powering up the automated stereotactic apparatus;

placing a proximal end of the automated stereotactic apparatus on a skin over a tissue object and visualizing the tissue object by an ultrasound transducer in an ultrasonographic display;

rotating an inner rotatable control knob connected to a pinion gear of a rack and pinion gear assembly so as to angulate an invasive tubular device slidably housed in the invasive tubular device assembly toward the tissue object until a linear shadow line in the ultrasonographic display crosses the tissue object, wherein the linear shadow line is produced by transmitting ultrasound waves from the ultrasound transducer across a linear movable pointer of a galvanometer electromagnetic pointing device;

displaying a numerical value of a distance between a proximal end of the invasive tubular device and the tissue object on a segment digital display of the power and electronic control assembly by turning on the segment digital display by rotating an outer rotatable control knob coaxially disposed with the inner rotatable control knob, wherein the tissue object is visualized as crossed by the linear shadow line in the ultrasonographic display;

locking a depth lock device in an invasive tubular device frame at a distance from the proximal end of the invasive tubular device, wherein the distance is the same as between the proximal end of the invasive tubular device and the tissue object visualized in the ultrasonographic display;

pushing in a lower half of an electric switch of a handle to generate a forward linear movement of the invasive tubular device so as to penetrate the tissue object;

pushing in an upper half of the electric switch of the handle to generate a backward linear movement of the invasive tubular device so as to retrieve a stylet through a tubular shaft of the invasive tubular device and to procure a tissue sample captured in a notch disposed thereof at a proximal end of the stylet;

detaching the invasive tubular device assembly from the powered propulsion assembly; and retrieving the tissue sample from the stylet and a bottom of the invasive tubular device frame.

10. A method of tissue sampling under ultrasonographic guidance, comprising;
providing the automated stereotactic apparatus of claim 2;
inserting the snap-fit ridges of the invasive tubular device frame into corresponding snap-fit notches of the powered propulsion assembly; and
releasing the snap-fit ridges of the invasive tubular device frame from the corresponding snap-fit notches of the powered propulsion assembly.

11. A method of tissue sampling under ultrasonographic guidance, comprising;
providing the automated stereotactic apparatus of claim 2;
obtaining a numerical value of the distance between the proximal end of the invasive tubular device and the tissue object on a segment digital display of the power and electronic control assembly by turning on the segment digital display by rotating an outer rotatable control knob coaxially disposed with an inner rotatable control knob, wherein the tissue object is visualized as crossed by the linear shadow line in the ultrasonographic display;
slidably moving the depth lock device over the invasive tubular device housed in the invasive tubular device frame to the distance from the proximal end of the invasive tubular device, wherein the distance is the same as between the proximal end of the invasive tubular device and the tissue object visualized in the ultrasonographic display; and
locking the depth lock device in the invasive tubular device frame by pressing down a lock and release lever of the depth lock device, wherein the lock and release lever of the depth lock device comprises a pair of protuberances, wherein the protuberances are configured to exert an outward pressure on the serrated inner longitudinal sidewalls when lowered into the open box shell of the invasive tubular device frame, and wherein the locking of the depth lock device inside the invasive tubular device frame prevents a forward movement of the tandem two-part coupling device beyond the depth lock device.

12. A method of tissue sampling under ultrasonographic guidance, comprising;
providing the automated stereotactic apparatus of claim 4;
placing a proximal end of the automated stereotactic apparatus on the skin over the tissue object and visualizing the tissue object in the ultrasonographic display;
rotating an inner rotatable control knob connected to the pinion gear of the rack and pinion gear assembly so as to pivot a linear propulsion gearbox frame about an aperture of a transverse shaft gear mount for a second transverse shaft gear device of a pivotable gearbox disposed thereof at a proximal end of the linear propulsion gearbox, wherein the linear propulsion gearbox frame coupleably carries the invasive tubular device frame thereof on an upper portion of the linear propulsion gearbox frame, and wherein the invasive tubular device frame slidably houses the invasive tubular device;
electronically registering a rotational displacement of the inner rotatable control knob by first electronic sensing device coaxially connected to the inner rotatable control knob to the power and electronic control assembly; and
radially moving a linear movable pointer of the galvanometer electromagnetic pointing device enclosed in a substantially ultrasound-transparent flat box disposed in front of a proximal portion of the ultrasound transducer by providing the galvanometer electromagnetic pointing device with a calculated electric voltage, current or resistance by the power and electronic control assembly based on the electronically registered rotational displacement of the inner rotatable control knob until the linear shadow line in the ultrasonographic display crosses the tissue object.

13. A method of tissue sampling under ultrasonographic guidance, comprising;
providing the automated stereotactic apparatus of claim 5; and
transmitting the ultrasound waves from the ultrasound transducer across the linear movable pointer at a right angle to the linear movable pointer, wherein the linear movable pointer comprises a material configured to block the ultrasound waves, and wherein the linear movable pointer is configured to reduce obtuse diffusion of rebounded ultrasound waves from the linear movable pointer.

14. A method of tissue sampling under ultrasonographic guidance, comprising;
providing the automated stereotactic apparatus of claim 7;
powering up the electric motor device;

delivering a rotational power from the electric motor device to the spur gearbox, wherein a cylindrical spur gear of the electric motor device meshes with the spur gearbox;

transmitting the rotational power from the spur gearbox to the longitudinal output shaft gear outside an ultrasound transducer enclosure, wherein the spur gearbox meshes with a distal portion of the longitudinal output shaft gear;

transmitting the rotational power from the longitudinal output shaft gear to the pivotable gearbox, wherein a proximal portion of the longitudinal output shaft gear meshes with a first transverse bevel gear of the first transverse shaft gear device of the pivotable gearbox;

transmitting the rotational power from the first transverse shaft gear device to a second transverse shaft gear device of the pivotable gearbox, wherein a first spur gear fixedly adjoining the first transverse bevel gear of the first transverse shaft gear device meshes with a second spur gear of the second transverse shaft gear device of the pivotable gearbox;

transmitting the rotational power from the second transverse shaft gear device to a planar bevel gear disposed on a proximal surface of a cylindrical spur gear of the pivotable gearbox; wherein a second transverse bevel gear of the second transverse shaft gear device meshes at a right angle with the planar bevel gear;

transmitting the rotational power from the cylindrical spur gear of the pivotable gearbox to the longitudinal rotatable gear shaft rotatably housed in the linear propulsion gearbox frame, whereby the longitudinal rotatable gear shaft rotates, wherein the cylindrical spur gear of the pivotable gearbox meshes with a longitudinal spur gear disposed thereof at a proximal portion of the longitudinal rotatable gear shaft; and converting a rotation of the longitudinal rotatable gear shaft to a linear movement of a linear propulsion device, wherein a helical gear of the longitudinal rotatable gear shaft meshes with internal helical threads of the linear propulsion device, and wherein a horizontal rail of the linear propulsion device slides in a longitudinal rail slot of the linear propulsion gearbox frame.

15. A method of tissue sampling under ultrasonographic guidance, comprising;

providing the automated stereotactic apparatus of claim 2;

powering up the automated stereotactic apparatus;

placing a proximal end of the automated stereotactic apparatus on the skin over the tissue object and visualizing the tissue object by an ultrasound transducer in the ultrasonographic display;

rotating an inner rotatable control knob connected to a pinion gear of a rack and pinion gear assembly so as to angulate the invasive tubular device slidably housed in the invasive tubular device assembly toward the tissue object until a linear shadow line in the ultrasonographic display crosses the tissue object;

displaying a numerical value of a distance between a proximal end of the invasive tubular device and the tissue object on the segment digital display of a power and electronic control assembly;

locking the depth lock device in the invasive tubular device frame at the distance from the proximal end of the invasive tubular device, wherein the distance is the same as between the proximal end of the invasive tubular device and the tissue object visualized in the ultrasonographic display;

pushing in a lower half of an electric switch of a handle to move forward a first part of a tandem two-part coupling device of the invasive tubular device, whereby a tubular shaft of the invasive tubular device slidably housing a stylet configured to penetrate the tissue, wherein the first part is reversibly locked with a second part located proximal to the first part of the tandem two-part coupling device, wherein a pivotable separator panel disposed on an upper portion of the first part reversibly locks the first part in a pivotable separator panel slot disposed on an upper portion of the second part of the tandem two-part coupling device, and wherein a proximal end of the first part is fixedly connected to a distal portion of the stylet and a proximal end of the second part of the second part of the tandem two-part coupling device is fixedly connected to the a distal portion of the tubular shaft;

unlocking the first part from the second part of the tandem two-part coupling device, whereby the first part collapses to the second part of the tandem two-part coupling device, whereby a tissue sampling notch thereof at the proximal end of the stylet advances through the tissue object, wherein the pivotable separator panel is pivotably lifted up from the pivotable separator panel slot upon a proximal border of the pivotable separator striking a ridge protruding from a distal border of an upper panel of the depth lock device; and pushing in an upper half of the electric switch of the handle to move backward the first part and the second part of the tandem two-part coupling device, whereby the tissue sampling notch of the stylet retrieves the tissue sample into the tubular shaft, wherein a compression spring disposed in between the first part and the second part of the tandem two-part coupling device extends to pull back the the stylet through the tubular shaft.

* * * * *